(12) United States Patent
Gluskin et al.

(10) Patent No.: US 9,683,924 B2
(45) Date of Patent: Jun. 20, 2017

(54) INFRASTRUCTURE CORROSION ANALYSIS

(75) Inventors: Mark A. Gluskin, Danville, CA (US);
Kevin C. Garrity, Dublin, OH (US);
Christopher M. Warner, Bend, OR (US); Alan Eastman, Sunol, CA (US);
Mark Reiboldt, Gardnerville, NV (US)

(73) Assignee: Quanta Associates, L.P., Houston, TX (US)

( * ) Notice: Subject to any disclaimer, the term of this patent is extended or adjusted under 35 U.S.C. 154(b) by 1128 days.

(21) Appl. No.: 13/464,729

(22) Filed: May 4, 2012

(65) Prior Publication Data

US 2012/0279599 A1     Nov. 8, 2012

Related U.S. Application Data

(60) Provisional application No. 61/482,538, filed on May 4, 2011, provisional application No. 61/598,192, filed on Feb. 13, 2012.

(51) Int. Cl.
*G01N 17/00* (2006.01)
*F17D 5/00* (2006.01)

(52) U.S. Cl.
CPC .............. *G01N 17/00* (2013.01); *F17D 5/00* (2013.01)

(58) Field of Classification Search
CPC .................................. F17D 5/00; G01N 17/00
USPC ....................................................... 702/184
See application file for complete search history.

(56) References Cited

U.S. PATENT DOCUMENTS

| 6,970,808 | B2 | 11/2005 | Abhulimen et al. |
| 2002/0158626 | A1* | 10/2002 | Shay .................... G01N 27/902 324/207.16 |
| 2005/0183028 | A1 | 8/2005 | Clough et al. |
| 2006/0068754 | A1* | 3/2006 | Goldfarb et al. ............. 455/410 |
| 2006/0129338 | A1* | 6/2006 | Turley et al. ................... 702/51 |
| 2006/0163165 | A1 | 7/2006 | Frank |
| 2009/0093916 | A1* | 4/2009 | Parsonnet et al. ............ 700/286 |
| 2009/0132089 | A1 | 5/2009 | Frank |
| 2009/0317293 | A1 | 12/2009 | Street et al. |
| 2010/0043074 | A1* | 2/2010 | Scates ............................. 726/25 |
| 2010/0088139 | A1 | 4/2010 | Rahi et al. |
| 2011/0018555 | A1* | 1/2011 | Meijer ................. G01N 27/028 324/652 |
| 2011/0301770 | A1* | 12/2011 | Rutman ........................ 700/292 |

OTHER PUBLICATIONS

Lee W. Young, International Search Report, Jun. 16, 2012, 2 pages, U.S. Patent and Trademark Office, U.S.

(Continued)

*Primary Examiner* — Ricky Ngon
(74) *Attorney, Agent, or Firm* — Mark A. Oathout; Oathout Law Firm

(57) ABSTRACT

The disclosure relates to systems, methods and apparatus for analyzing an infrastructure system including measurement of a parameter associated with the infrastructure system, electronically recording the measured parameter as a data, transferring the data to an infrastructure unit which may be remote from the infrastructure system, analyzing the data to generate a risk model, and predicting a characteristic of the infrastructure system according to the risk. An implementation plan may be generated, and/or maintenance services may be performed as per the characteristic that is predicted.

6 Claims, 40 Drawing Sheets

(56) References Cited

OTHER PUBLICATIONS

Lee W. Young, Written Opinion of the International Searching Authority, Jun. 16, 2012, 7 pages, U.S. Patent and Trademark Office, U.S.
Olivier Couteau, Supplementary European Search Report, Aug. 13, 2014, 7 pages, European Patent Office, The Hague, Netherlands.
Oliver Moghissi, et al., Internal Corrosion Direct Assessment of Gas Transmission Pipelines—Methodology, Final Report, GTI Contract No. 8329, Apr. 1, 2002, 41 pages, Des Plaines, IL, United States of America.
Aida Lopez-Garrity et al., Application of Corrosion Growth and Analysis in Support of Direct Assessment Reassessment Intervals, Mar. 12, 2006, 18 pages, NACE International, Houston, TX, United States of America.
Hermann Dellwing, et al., Power System Survivability Increase with Intelligent Support Tools. Power & Energy Society General Meeting, 2009. PES '09. IEEE, Jul. 23-30, 2009, 6 pages, IEEE, Calgary, AB, Canada.
Kang Lin, et al., PRA for vulnerability assessment of power system infrastructure security, Power Symposium, 2005. Proceedings of the 37th Annual North American, Oct. 23-25, 2005, pp. 43-51, IEEE, Ames, IA, United States of America.
Jose Luis Salazar Lopez, Dirección De Nuevas Creaciones, Aug. 19, 2014, 17 pages, Superintendencia De Industria Y Comercio, Bogotá, Colombia.

\* cited by examiner

| Classification | Resistivity (Ω-cm) |
|---|---|
| Extremely Corrosive | <500 |
| Very Corrosive | 500 to 1,000 |
| Corrosive | 1,000 to 10,000 |
| Mildly Corrosive | 10,000 to 20,000 |
| Progressively Less Corrosive | >20,000 |

| Degradation Classification | Degree of Corrosion | Visual Description |
|---|---|---|
| 6 | 6 Extremely severe expect 50% to 100% metal loss | Extreme amount of scale greater than 1/2" thick with reported nodules and other indications of severe degradation |
| 5 | Severe expect 40% to 70% metal loss | Scale up to 1/2" thick with severe pitting reported |
| 4 | Moderate to severe expect 30 to 50% metal loss | Up to 50% reported metal loss |
| 3 | Moderate corrosion expect 10% to 40% | Up to 3/8" scale reported |
| 2 | Minor corrosion up to 10% metal loss | General corrosion and pitting less than 10 mils |
| 1 | No corrosion to minor corrosion | Zinc coating still intact in some places below grade |

*FIG. 4D*

| Data Element | Purpose | Performed at each leg | Units of Measure | Criteria |
|---|---|---|---|---|
| GPS Coordinates | To record the global position of each tower, to identify potential trends in degradation vs. geographical position | No | Degree, Minutes, seconds | Sub-meter |
| AC Tower to Soil Potential | To identify any shock hazards | Yes | Volts | <15 |
| DC Tower to Soil Potential | To provide a qualitative indication the degree of loss of the galvanized coating on the buried structure | Yes | Volts | <-0.8 |
| LPR Corrosion Rate Measurement | To determine the relative corrosion rate of the soil | No | 0.001"/yr | None |
| Visual Corrosion Pattern | To describe the pattern and extent of corrosion on the grillage | Yes | text | None |
| Section Loss Length | The Length of the corrosion observed | Yes | Inches | None |
| Maximum Pit Depth | Measure the depth of localized corrosion | Yes | 0.001 inches | See Fig. 4A |
| Antimony Cell pH | Measure the acidity of the soil to help determine the propensity for corrosion | Yes | Unit less | |
| Redox Potential | Measure the oxidation-reduction potential of the soil that can be an indicator of microbiological corrosion | No | mV | Moderate<150 Severe<0 |
| Coating Thickness 12" above the soil | Measure of the zinc coating metal that has been exposed to the atmospheric conditions for close to 40 years. | Yes | 0.001 inches | None |
| Coating Thickness 12" below the soil | Measure of the remaining zinc coating metal remaining after 40 years of exposure to soil | Yes | 0.001 inches | None |
| Soil Resistivity | Measure the soil resistivity of the soil at 1',2', and 3' depths. Soil resistivity can be an indicator of corrosivity of the soil | No | Ω-cm | See Fig. 4D |
| Soil Type | Record the soil type. Different soil types have inherently different propensity to cause corrosion | Yes | Text | None |
| Topography | Record the type of slope the tower is on. The topography can influence drainage and ground water level | No | Text | None |
| Vegetation | The type and level of vegetation can be an indicator of overall soil moisture and level of cations and anions in the soil. | No | Text | None |
| Photography | Record the visual appearance of each leg, soil appearance and vegetation type. | Yes | None | None |
| Comments | Record visual observations of the degree of urethane and zinc coating degradation as well as the amount of exfoliation of the steel | Yes | None | None |

Corrosion Condition Assessment Demonstration Project
High Voltage Transmission Tower Legs

| Circuit: | ACDM-2 | | Date: | 11/9/2010 |
|---|---|---|---|---|
| Tower ID: | 176 | | Topo: | See Comments |
| Type: | 375kV | | Reader: | BAL/CII |
| Company: | | | Weather: | Humid ~85°F, Sunny |
| Safety Check Wires | ☑ Yes | | Soil: | Sandy clay |
| Safety Check Conductors | ☑ Yes | | Tower ID Image # | |
| Safety Check Fluke | ☑ Yes | | Overall Tower Digital Image # | |

Current Flow: A, B, C, D (diagram), N

| | Digital Image # | Location/ Depth | AC Potential (VAC) | DC Potential (VDC) | pH Antimony Cell | LPR Imbalance | LPR Corr. | Redox | Zinc Coating 12" Above | Zinc Coating 12" Below | Metal Loss |
|---|---|---|---|---|---|---|---|---|---|---|---|
| Leg A | | Grade | 0.000 | -0.495 | 5 | 0.24 | 2.56 | 397.6 | 2.15 | N/A, to much corrosion scale to measure | See Additional Details below |
| | | 9" | | -0.504 | 4.5 | | | | | | |
| | | 18" | | -0.519 | 4.5 | | | | | | |
| | | Remote(30) | | -0.535 | N/A | | | | | | |
| Leg B | | Grade | 0.000 | -0.500 | 5 | 0.24 | 3.17 | 384.4 | 2.98 | N/A, to much corrosion scale to measure | See Additional Details below |
| | | 9" | | -0.507 | 4.5 | | | | | | |
| | | 18" | | -0.586 | 4.5 | | | | | | |
| Leg C | | Grade | 0.000 | -0.482 | 5 | 0.15 | 3.39 | 369.9 | 1.99 | N/A, to much corrosion scale to measure | See Additional Details below |
| | | 9" | | -0.422 | 4.5 | | | | | | |
| | | 18" | | -0.442 | 4 | | | | | | |
| Leg D | | Grade | 0.000 | -0.446 | 5 | 0.69 | 3.62 | 398.9 | 2.04 | N/A, to much corrosion scale to measure | See Additional Details below |
| | | 9" | | -0.429 | 4.5 | | | | | | |
| | | 18" | | -0.439 | 4 | | | | | | |

| Soil Resistivity | 1 foot | 2 feet | 3 feet |
|---|---|---|---|
| Resistance | 2.7 | 1.8 | 1 |
| Multiplier | 100 | 100 | 100 |

| Soil Sample ID | |
|---|---|
| A | ADCM 2 176Leg A |
| B | ADCM 2 176Leg B |
| C | ADCM 2 176Leg C |
| D | ADCM 2 176Leg D |

Comments: Typography - ~45 Slope heading to the west. Tower is located on side of ~500 foot tall hill, jungle growth ~3 feet tall in height, Rural Area, well drained. Galvanized costing

| Additional Details-Metal Loss | |
|---|---|
| Leg A | |
| Leg B | |
| Leg C | |
| Leg D | |

| Degradation Classification | Total Risk Score Range | Degree of Corrosion | Visual Description |
|---|---|---|---|
| 6 | >1200 | Extremely severe expect 50% to 90% wall loss | Extreme amount of scale greater than 1/2" thick with reported nodules and other indications of severe degradation |
| 5 | 1150 to 1250 | Severe expect 30% to 70% wall loss | Scale up to 1/2" thick with severe pitting reported |
| 4 | 1000 to 1175 | Moderate to severe expect 30 to 50% metal loss | Up to 50% reported metal loss |
| 3 | 900 to 1050 | Moderate corrosion expect 10% to 40% wall loss | Up to 3/8" scale reported |
| 2 | 780 to 900 | Minor corrosion up to 10% wall loss | General corrosion and pitting less than 10 mils |
| 1 | <780 | No corrosion to minor corrosion | Zinc coating still intact in some places below grade |

*FIG. 9*

| Circuit | By Tower | | By Leg | | | | Comments |
|---|---|---|---|---|---|---|---|
| | Avg. of Degr. | Total Risk Index | Leg | Risk Score | Degr Rating | Figure # | |
| ADCM-2-165 | 2.3 | 907 | A | 221 | 1 | 3.1 | No appreciable corrosion. |
| | | | B | 263 | 2 | | |
| | | | C | 216 | 3 | | |
| | | | D | 207 | 3 | | |
| ADCM-2-176 | 2.5 | 999 | A | 216 | 2 | | |
| | | | B | 211 | 2 | | |
| | | | C | 286 | 2 | 3.2 | Minor surface rusting |
| | | | D | 286 | 4 | 3.3 | Up to 50% metal loss on some cross members |
| RMLA-1 & 2-42 | 3.0 | 972 | A | 207 | 3 | | |
| | | | B | 263 | 3 | | |
| | | | C | 286 | 3 | | |
| | | | D | 216 | 3 | | |
| RMLA 1 & 2-61 | 3.3 | 1056 | A | 221 | 3 | | |
| | | | B | 211 | 4 | 3.4 | Severe localized attack at the soil/air interface |
| | | | C | 286 | 3 | | |
| | | | D | 338 | 3 | | |
| ADCM-2-156 | 4.0 | 913 | A | 263 | 2 | | |
| | | | B | 221 | 6 | 3.5 | Up to 100% metal loss with cracking the remaining ligament of the cross |
| | | | C | 191 | 4 | | |
| | | | D | 238 | 4 | | |
| ADCM-1-153 | 4.3 | 1056 | A | 261 | 4 | | |
| | | | B | 186 | 5 | 3.6 | |
| | | | C | 271 | 4 | | |
| | | | D | 338 | 4 | 3.7 | |
| ADCM-1-174 | 4.3 | 1149 | A | 291 | 4 | 3.8 | Up to 50% metal loss on some cross members |
| | | | B | 286 | 6 | 3.9 | 100% metal loss on some cross members |
| | | | C | 286 | 5 | 3.10 | Over 50% metal loss on some cross members |
| | | | D | 286 | 2 | 3.11 | |
| RMLA 1 & 2-41 | 5.0 | 1455 | A | 438 | 5 | | |
| | | | B | 338 | 5 | | |
| | | | C | 263 | 5 | 3.12 | 1/2" thick corrosion deposits |
| | | | D | 416 | 5 | | |

FIG. 11

| Circuit | By Tower | Projected Degradation Classification | | |
|---|---|---|---|---|
| | Avg. of Degr. | 2013 | 2015 | 2023 |
| ADCM-2-165 | 2.3 | 2.62 | 2.86 | 3.47 |
| ADCM-2-176 | 2.5 | 3.01 | 3.35 | 4.20 |
| RMLA 1 & 2-42 | 3.0 | 3.45 | 3.75 | 4.51 |
| RMLA 1 & 2-61 | 3.3 | 3.59 | 3.82 | 4.39 |
| ADCM-2-156 | 4.0 | 4.68 | 5.13 | 6.26 |
| ADCM-1-153 | 4.3 | 4.71 | 5.01 | 5.78 |
| ADCM-1-174 | 4.3 | 5.01 | 5.51 | 6.78 |
| RMLA 1 & 2-41 | 5.0 | 5.74 | 6.23 | 7.46 |

*FIG. 12*

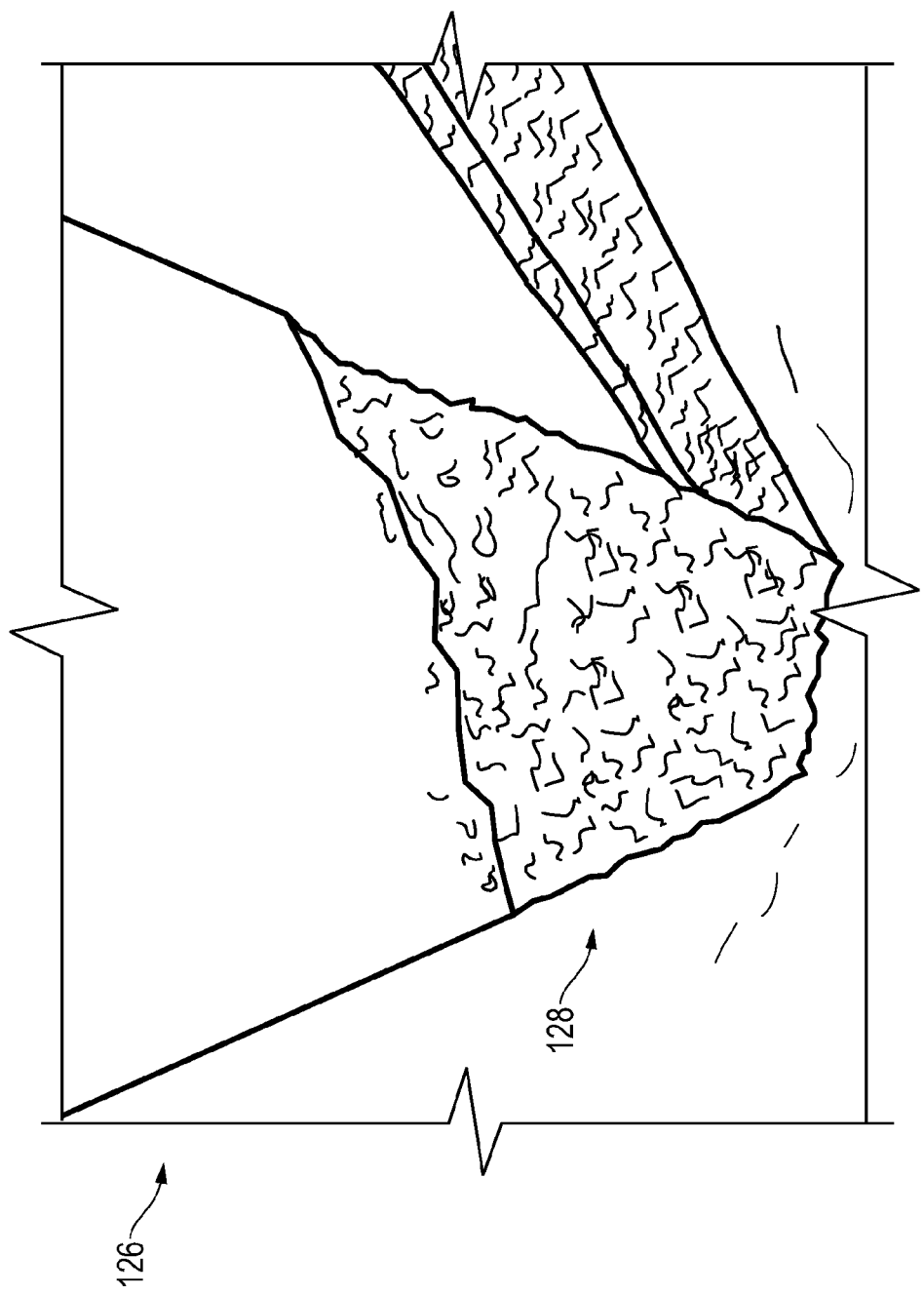

| DA/ILI | DA | ILI |
|---|---|---|
| Route Number | N-Segment | ILI Log Distance (Ft.) |
| Examination Date | IMA Number | RMP-11 Ref. Section |
| Mile Point | Region Number | Reference Girth Weld |
| Exam Performed by | Sub-region # (ICDA) | Dist. From Girth Weld |
| Project manager | Stationing | |
| Order Number | | |

Excavation Details

| | | | |
|---|---|---|---|
| Excavation Priority | Scheduled | Excavation Reason | ILI |
| P/S or CIS reads before excavation (ON Reading) mV | 0 | P/S or CIS (OFF Reading) mV | 0 |
| P/S or CIS Comments | CIS not performed | | |
| Actual Inspection Length (Ft.) | 5.17 | Nominal Wall Thickness (In.) | 0.219 |
| Planned Inspection Length (Ft.) | 5 | Nominal Pipe Diameter (In.) | 12 |
| GPS File Name | DIG 31 | | |
| Planned Ceterline GPS Coordinates (Based on GIS)-Nothing | 0 | | |
| Planned Ceterline GPS Coordinates (Based on GIS)-Easting | 0 | | |
| Planned Ceterline GPS Coordinates (Based on GIS)-Latitude | 39° 0' 53.71" | | |
| Planned Ceterline GPS Coordinates (Based on GIS)-Longitude | 123° 7' 32.66" | | |
| Ceterline GPS Coordinates (Uncorrected Field Measurement)-Northing | 4318440.831 | | |
| Ceterline GPS Coordinates (Uncorrected Field Measurement)-Easting | 489113.697 | | |
| Ceterline GPS Coordinates (Corrected Field Measurement)-Northing | 4318439.244 | | |
| Ceterline GPS Coordinates (Corrected Field Measurement)-Easting | 489113.869 | | |

Data Before Coating Removal

Site Data

| | | | |
|---|---|---|---|
| Primary Native Soil Type | Clay | Mixed Soil Types Explanation | With Loam |
| Backfill Material as found | Native | Depth of Cover (Ft.) | 6.33 |
| Backfill Comments | N/A | | |
| Is Rock Shield present? | N | | |
| Coating Type | HAA | Additional Coatings Found | None |
| Coating Type Comments | N/A | | |
| Coating Thickness (In.) | 0.14 | Number of Coating Layers | 1 |
| Holiday Testing Performed | Y | Holiday Testing Voltage Used VOLTS | 2000 |
| Holiday Testing Device Used | Coil | | |
| Holiday Testing Comments | N/A | | |
| Soil Sample Location | Upstream Edge Adjacent to the pipe | | |
| Location notes | | | |
| Ground Water Present | N | Sample Collected | N |
| Sample pH | 0 | | |
| Coating Conditions | Good-Adhered to Pipe | | |
| Coating Conditions Comments | Removed before DE Tech onsite. | | |
| Coating Degradation Map Zero Reference Point | Upstream Edge of Coating Removal | Photos Taken | Y |

*FIG. 17A*

| DA/ILI | DA | ILI |
|---|---|---|
| Route Number | N-Segment | ILI Log Distance (Ft.) |
| Examination Date | IMA Number | RMP-11 Ref. Section |
| Mile Point | Region Number | Reference Girth Weld |
| Exam Performed by | Sub-region # (ICDA) | Dist. From Girth Weld |
| Project manager | Stationing | |
| Order Number | | |

| | | Location of Coating Sample | Adjacent to the Dent. |
|---|---|---|---|
| Coating Sample Taken | Y | If Yes, pH of Liquid | 0 |
| Liquid Underneath Coating | N | If Yes, Corrosion Sample Taken | N |
| Corrosion Product Present | N | | |
| Corrosion Comments | N/A | | |
| Soil pH (Sb Electrode) Upstream | 5.4 | Soil pH (Sb Electrode) Downstream | 5.4 |

Coating Damage

| No. | Feet from Reference | O'clock | Max. Length (In.) | Max. Circuit Extent (In.) |
|---|---|---|---|---|
| | | | | |

Map of Coating Degradation

Soil Resistivity

| | | | |
|---|---|---|---|
| Pipe to Soil Potential in Ditch (-mV)-Upstream | -930 | Pipe to Soil Potential in Ditch (-mV)-Downstream | -982 |
| Pipe to Soil Potential in Ditch (-mV)-Comments | N/A | | |
| Soil Resistivity in Ditch -4-Pin Multiplier | 1 | Soil Resistivity in Ditch -4-Pin (Ohms) | 6.83 |
| 4-Pin Spacing Distance in Whole Feet | 4 | 4-Pin Resistivity | 5231.78 |
| Soil Box Multiplier | 1000 | Soil Box Reading Ohms | 3 |
| Soil Box Resistivity | 3000 | | |

Data After Coating Removal

| | | | |
|---|---|---|---|
| Pipe Temperature(F) | 64 | | |
| Weld Seam Type | ERW | Measured Pipe Diameter (In.) | 12.75 |
| Weld Seam Type (3rd Weld) | N/A | Weld Seam Type (2nd Weld) | N/A |
| Girth Weld Coordinates: Northing | 0 | Girth Weld Coordinates: Easting | 0 |
| Girth Weld Elevation (m) | 0 | | |
| Seam Weld O'clock Position | 11 | Seam Weld O'clock Position (2nd Weld) | N/A |
| Seam Weld O'clock Position (3rd Weld) | N/A | | |
| Corrosion Damage | N | Mechanical Damage | Y |
| Other Damage Notes | Dent caused by mech damage. | | |
| Wet Fluorescent Mag. Part. Test Performed? | Y | Were there any linear indications? | N |
| Wet Fluorescent Mag. Part. Comments | No indications found | | |
| UT Wall Thickness Measurement-TDC (in.) | 0.23 | UT Wall Thickness Measurement-1 O'clock (in.) | 0.23 |
| UT Wall Thickness Measurement-2 O'clock (in.) | 0.23 | UT Wall Thickness Measurement-3 O'clock (in.) | 0.23 |
| UT Wall Thickness Measurement-4 O'clock (in.) | 0.229 | UT Wall Thickness Measurement-5 O'clock (in.) | 0.23 |
| UT Wall Thickness Measurement-6 O'clock (in.) | 0.231 | UT Wall Thickness Measurement-7 O'clock (in.) | 0.229 |
| UT Wall Thickness Measurement-8 O'clock (in.) | 0.23 | UT Wall Thickness Measurement-9 O'clock (in.) | 0.23 |
| UT Wall Thickness Measurement-10 O'clock (in.) | 0.23 | UT Wall Thickness Measurement-11 O'clock (in.) | 0.23 |

*FIG. 17B*

| DA/ILI | DA | ILI |
|---|---|---|
| Route Number<br>Examination Date<br>Mile Point<br>Exam Performed by<br>Project manager<br>Order Number | N-Segment<br>IMA Number<br>Region Number<br>Sub-region # (ICDA)<br>Stationing | ILI Log Distance (Ft.)<br>RMP-11 Ref. Section<br>Reference Girth Weld<br>Dist. From Girth Weld |

Nominal Wall Thickness (in.) 0.219

External Corrosion Mapping

| Anomaly | Point | Inches from Ref. | Inches from TDC | Cell Length | Cell Width | Max. Pit Depth | Description/Notes |
|---|---|---|---|---|---|---|---|
| 2 | 10 | 5 | 5 | | | | |

Overview Map of Corroded Area

External Pit Depth

| Anomaly | Point | Inches from Ref. | Inches from TDC | Description/Notes |
|---|---|---|---|---|
| 1 | 1 | | ROW:1 | |

External Pit Depth Measurement Grid

Internal Pit Depth

| Anomaly | Point | Inches from Ref. | Inches from TDC | Description/Notes |
|---|---|---|---|---|
| | | | | |

Internal Pit Depth Measurement Grid

Recoat Data

CLIENT Representative Approved to Proceed with Recoat   Y                Foreman Approved to Proceed with Recoat   Y Sandblast Media   Clean Blast
Pipe Recoated With   Protal 7200                          Anchor Profile Measurement (mils)   3.1
Recoat Comments   N/A
Air Temperature (F)   69                                  Pipe Temperature (F)   69
Time of Day   10                                          Dew Point (F)   61
Relative Humidity (%)   75                                Repair Coating Hardness (if ARC Coating)   N/A
Measured Coating Thickness-3:00 (mils)   34               Measured Coating Thickness-6:00(mils)   31
Measured Coating Thickness-9:00 (mils)   34               Measured Coating Thickness-12:00(mils)   34
Holiday Tested   Y                                        Holiday Test Device Used   Coil
Voltage Used for Holiday Testing (Volts)   2000
Coupon Test Station Installed   N                         ETS Installed   N
If Yes, Date Installed
Surface Configuration   Other
Surface Configuration Comments   Not Installed.
Backfill Material   Sand

*FIG. 17C*

| DA/ILI | DA | ILI |
|---|---|---|
| Route Number | N-Segment | ILI Log Distance (Ft.) |
| Examination Date | IMA Number | RMP-11 Ref. Section |
| Mile Point | Region Number | Reference Girth Weld |
| Exam Performed by | Sub-region # (ICDA) | Dist. From Girth Weld |
| Project manager | Stationing | |
| Order Number | | |

Backfill Material Comments   Sand and native soil
                                      Coating Protection   None
Pipe-to-Soil Reading Over Bell Hole After Backfill (mV)   0
            Post Backfill Pipe-to-Soil Reading Comments

Repair Data

Repair Made   N                        Number of Repairs Made   0
                     Repair Type   N/A                      Damage Repaired
Misc. Comments/Information   Small dent with no repair required.

*FIG. 17D*

| DA/ILI | DA | ILI |
|---|---|---|
| Route Number<br>Examination Date<br>Mile Point<br>Exam Performed by<br>Project manager<br>Order Number | N-Segment<br>IMA Number<br>Region Number<br>Sub-region # (ICDA)<br>Stationing | ILI Log Distance (Ft.)<br>RMP-11 Ref. Section<br>Reference Girth Weld<br>Dist. From Girth Weld |

Magnetic Particle Examination

| | | | |
|---|---|---|---|
| Magnetic Particle Examination Date | | | |
| Test Equipment | Yoke | Serial No. | 10234 |
| Technique | AC-Continuous | Test Medium | Wet-Fluorescent |
| Quality Control Batch #s | A9F001 | | |
| Surface Condition | As Blasted<br>NACE 2 | Reference GPS: Easting | 0 |
| Reference GPS: Northing | 0 | Mag. Results Accepted | Y |
| Acceptance Criteria | No linear<br>indications | | |

Magnetic Particle Anomaly Table

| Anomoly | Inches from Ref. | Inches from TDC | Length(In.) | Remain. Wall | Indication Removed/Notes | Link |
|---|---|---|---|---|---|---|
| | | | | | | |

| | | | |
|---|---|---|---|
| Technician Name | | Level | |
| Assistant | N/A | Level | |
| Comments | | | |

*FIG. 17E*

| DA/ILI | DA | ILI |
|---|---|---|
| Route Number<br>Examination Date<br>Mile Point<br>Exam Performed by<br>Project manager<br>Order Number | N-Segment<br>IMA Number<br>Region Number<br>Sub-region # (ICDA)<br>Stationing | ILI Log Distance (Ft.)<br>RMP-11 Ref. Section<br>Reference Girth Weld<br>Dist. From Girth Weld |

Photo Log

| Photo # | Axial | Orientation | Description/Comments |
|---|---|---|---|
| | | | |

*FIG. 17F*

| DA/ILI | DA | ILI |
|---|---|---|
| Route Number | N-Segment | ILI Log Distance (Ft.) |
| Examination Date | IMA Number | RMP-11 Ref. Section |
| Mile Point | Region Number | Reference Girth Weld |
| Exam Performed by | Sub-region # (ICDA) | Dist. From Girth Weld |
| Project manager | Stationing | |
| Order Number | | |

Site Map

| Notes | |

[Insert satellite, aerial or other map from qualified source, e.g., GOOGLE Earth]

FIG. 18F

INFRASTRUCTURE CORROSION ANALYSIS

CROSS-REFERENCE TO RELATED APPLICATIONS

This application claims the benefit of U.S. Provisional Application No. 61/482,538 filed May 4, 2011, and of U.S. Provisional Application No. 61/598,192 filed Feb. 13, 2012.

STATEMENTS REGARDING FEDERALLY SPONSORED RESEARCH OR DEVELOPMENT

Not Applicable.

NAMES OF THE PARTIES TO A JOINT RESEARCH AGREEMENT

Not Applicable.

REFERENCE TO A "SEQUENCE LISTING", A TABLE, OR A COMPUTER PROGRAM

Not Applicable.

BACKGROUND

Energy infrastructure such as transmission towers and pipelines may be installed to provide energy and other services to houses, buildings, facilities and other structures. Once installed it is difficult to determine if there is a maintenance problem with the buried infrastructure and whether a maintenance and/or remediation operation should be performed on the infrastructure, or portions thereof. Therefore a need exists to efficiently perform testing, inspection, and analysis of buried energy infrastructure.

BRIEF SUMMARY

The disclosure relates to systems, methods and apparatus for analyzing an infrastructure system including measurement of a parameter associated with the infrastructure system, electronically recording the measured parameter as a data, transferring the data to an infrastructure unit which may be remote from the infrastructure system, analyzing the data to generate a risk model, and predicting a characteristic of the infrastructure system according to the risk. An implementation plan may be generated, and/or maintenance services may be performed as per the characteristic that is predicted.

As used herein the term "determine" and the like shall inclusive of the meaning of "infer" and the like.

As used herein the term "fluids" shall include fluids and gases.

BRIEF DESCRIPTION OF THE SEVERAL VIEWS OF THE DRAWING

The embodiments may be better understood, and numerous objects, features, and advantages made apparent to those skilled in the art by referencing the accompanying drawings. These drawings are used to illustrate only typical embodiments of this invention, and are not to be considered limiting of its scope, for the invention may admit to other equally effective embodiments. The figures are not necessarily to scale and certain features and certain views of the figures may be shown exaggerated in scale or in schematic in the interest of clarity and conciseness.

FIG. 4D depicts a degradation classification.

FIG. 5 depicts a table of data elements collected during a data collection stage.

FIG. 6 depicts an example of a data collection sheet.

FIGS. 8A and 8B depict a portion of a visual display from the infrastructure unit.

FIG. 9 depicts a correlation of risk score and degradation classification created by the risk analysis unit of the infrastructure unit.

FIG. 11 depicts a table listing of photos taken at the energy infrastructure 102 of amounts of degradation in the legs.

FIG. 12 depicts a table generated by the infrastructure unit that depicts the projected degradation classification for each transmission tower.

FIGS. 13A-13D depict photos of portions of the energy infrastructure.

FIGS. 17A-17H depict an example of a report used in conjunction with the pipeline analysis system according to an embodiment.

FIGS. 18A-18H depict screenshots of a visual display from the infrastructure unit.

DETAILED DESCRIPTION OF EMBODIMENT(S)

The description that follows includes exemplary apparatus, methods, techniques, and instruction sequences that embody techniques of the inventive subject matter. However, it is understood that the described embodiments may be practiced without these specific details.

Embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the inventive subject matter may take the form of a computer program product embodied in any tangible medium of expression having computer usable program code embodied in the medium. The described embodiments may be provided as a computer program product, or software, that may include a machine-readable medium having stored thereon instructions, which may be used to program a computer system (or other electronic device(s)) to perform a process according to embodiments, whether presently described or not, since every conceivable variation is not enumerated herein. A machine readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. In addition, embodiments may be embodied in an electrical, optical, acoustical or other form of propagated signal (e.g., carrier waves, infrared signals, digital signals, etc.), or wireline, wireless, or other communications medium.

Computer program code for carrying out operations of the embodiments may be written in any combination of one or more programming languages, including an object oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection may be made to an external computer (for example, through the Internet using an Internet Service Provider).

Figure 1:
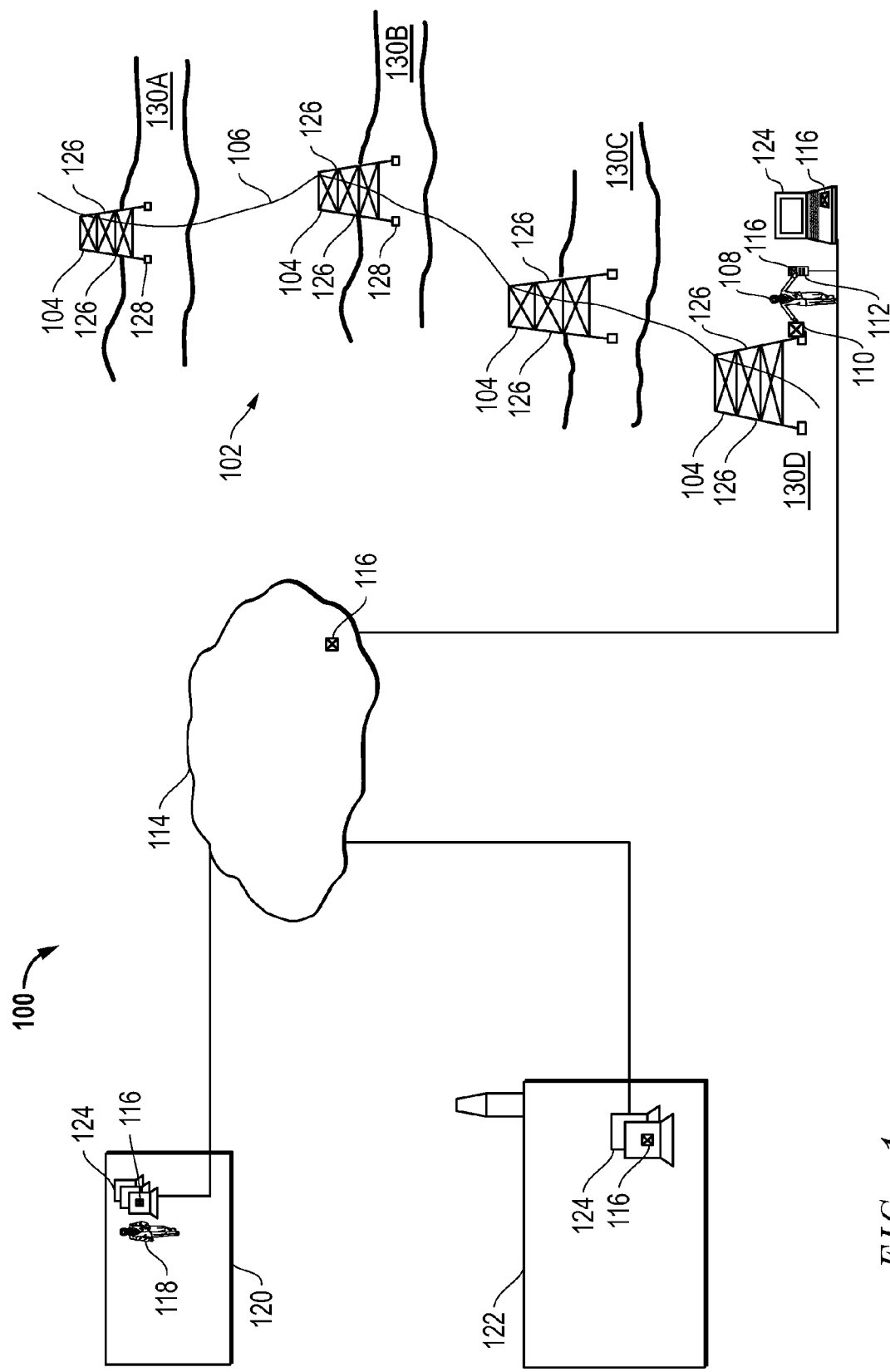
FIG. 1 depicts a schematic view of an infrastructure analysis system.

FIG. 1 depicts a schematic view of an infrastructure analysis system 100. The infrastructure analysis system 100 may be for analyzing conditions and/or damage to a power infrastructure 102. As shown the infrastructure analysis system 100 is a plurality of transmission towers 104 for supporting a transmission line 106. The infrastructure analysis system 100 may have the power infrastructure 102, one or more field workers 108, one or more data collection tools 110, one or more data input devices 112, a communication network 114 and an infrastructure unit 116. In addition the infrastructure analysis system 100 may have one or more analysis workers 118 at a service company 120. The service company 120 may be hired to perform analysis, maintenance, remediation, and/or construction on the power infrastructure 102. Further, the infrastructure analysis system 100 may communicate with a client company 122. The service company 120 and/or the client company 122 may have any number of computers 124 which may have the infrastructure unit 116 therein. In addition to, or as an alternative to, the one or more data input devices 112, the field worker may have a computer 124.

Figure 2A:
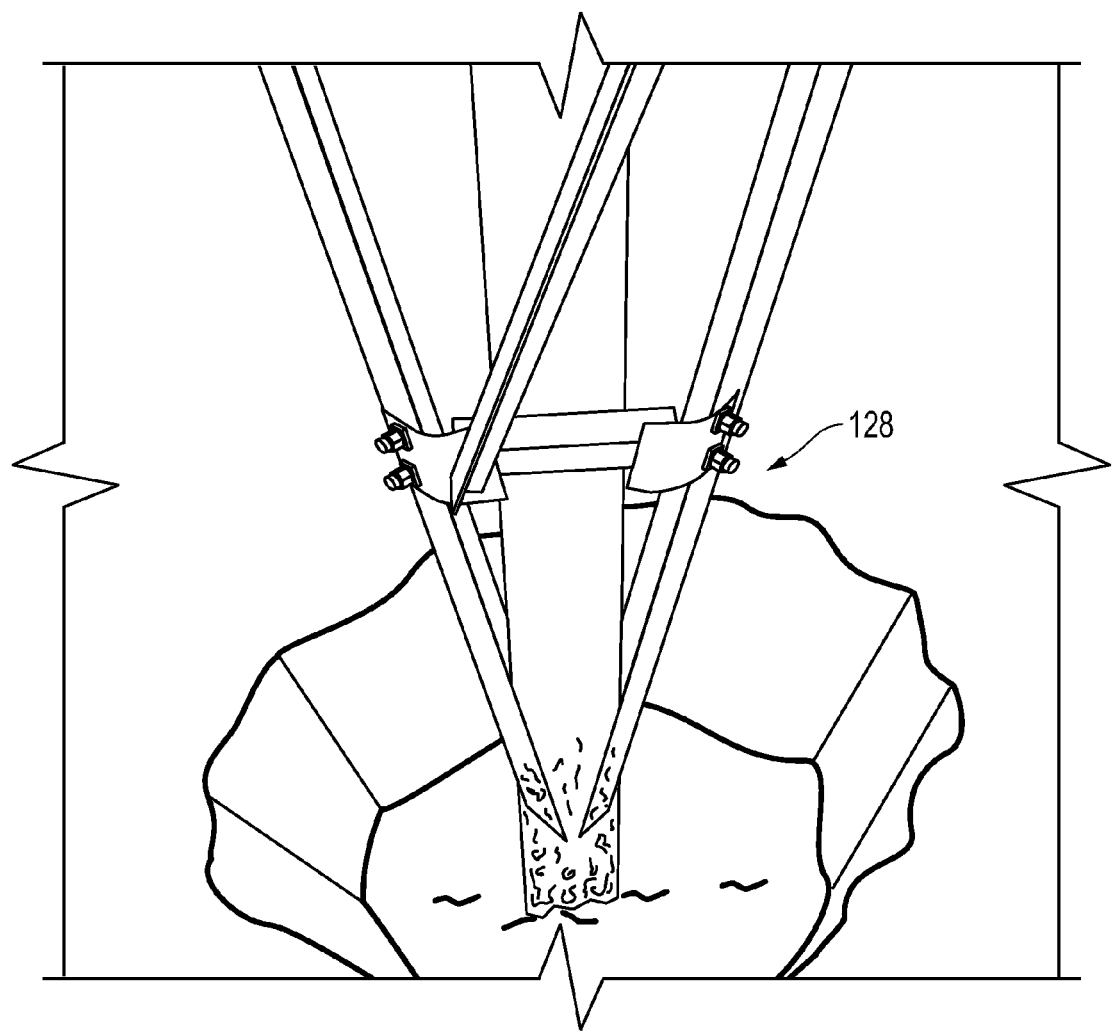
FIGS. 2A and 2B depict a view of a tower footing according to one embodiment.
Figure 2B:
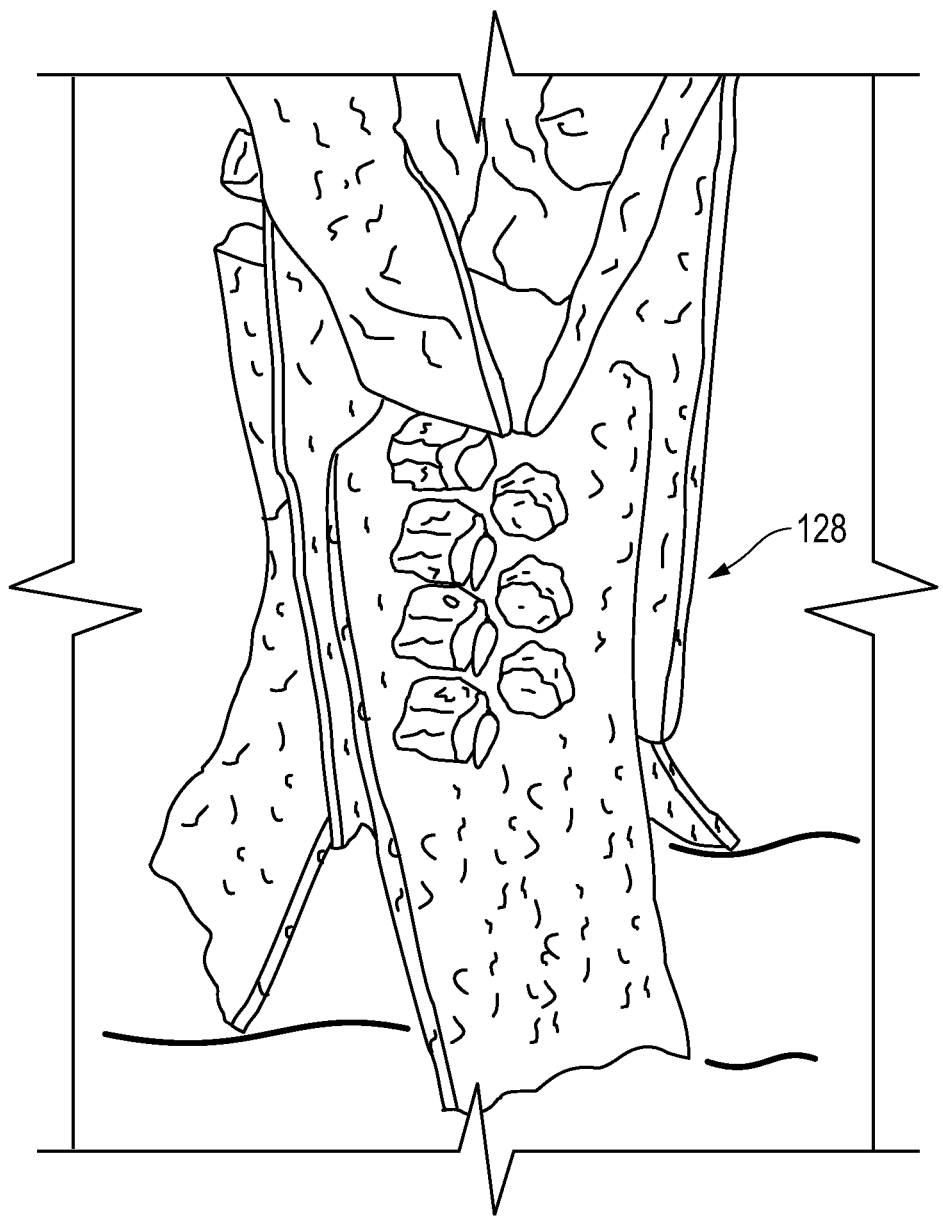

The transmission towers 104 may be any suitable transmission towers or transmission line supports. The transmission towers 104 may have one or more legs 126 and one or more tower footings 128. The tower footings 128 may secure into a soil 130(A-D) for securing the transmission tower 104 in place. The tower footings 128 may secure to the legs 126 or be integral therewith. The tower footing 128 may be steel member foundations having multiple components as shown in FIGS. 2A and 2B. The soil 130A-D at each of the transmission towers 104 may be similar or may vary at each transmission tower 104 or at each leg 126.

The field worker 108 may be any suitable worker (such as a technician or an engineer) that is sent to the power infrastructure 102 to collect data during a data collection phase of the project. The field worker 108 may input the collected data directly into the one or more data input devices 112 and/or the computer 124 as the data is collected in the field. The one or more data collection tools 110 may communicate directly with the one or more data input devices 112 and/or the computer 124 or the field worker 108 may input the collected data manually. As the data is collected, the one or more data input devices 112 and/or the computer 124 may send the data to the infrastructure unit(s) 116 located about the infrastructure analysis system 100. The field worker 108 may collect data for one of the transmission towers 104 then move to the next transmission towers 104, or selected transmission towers 104, in the power infrastructure 102. Further, the field worker 108 may collect data from only a select few of the transmission towers 104 and then use the infrastructure analysis system 100 to predict the conditions of the other transmission towers 104 and formulate a project plan, or implementation plan.

The communication network 114 allows for communication about the infrastructure analysis system 100 and may be any suitable network including those described herein.

Figure 3A:
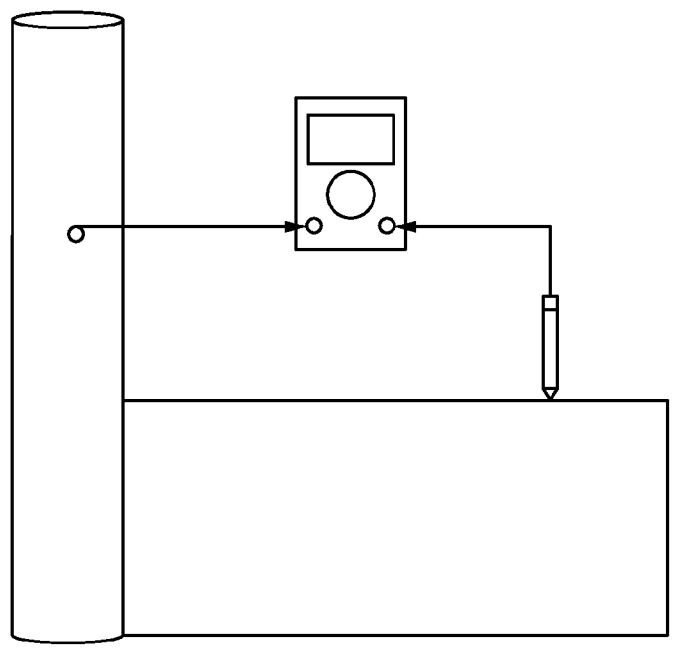
FIGS. 3A and 3B depict a schematic view of data collection systems or methods.

The field worker 108 may collect data from all, or portions of, the power infrastructure 102 during a data gathering phase of the project. During the data gathering phase the field worker 108 may use the data collection tools 110 and/or observation at the power infrastructure 102. The data collection may take place during routine structure surveys including, but not limited to, annual surveys, scheduled maintenance, specific service calls and the like. The data collection may include identifying candidate areas for detailed surveys, measuring DC and AC structure potential to a Copper-Copper Sulfate Electrode (CSE). The electrochemical potential of a structure (for example the transmission tower) may be related to corrosion activity. For example the potential of carbon steel may be −0.550V to −0.800V (CSE). The potential of newer structures is more electronegative. The potential of coated structures may be more electronegative. The potential of steel embedded in concrete 0.250 to −0.550V (CSE). The potential of galvanized structures −0.800V (CSE) and the potential of copper is −0.200V to −0.300V (CSE). Therefore the data collection may include measuring the potential of the tower to soil as shown in FIG. 3A.

Figure 3B:
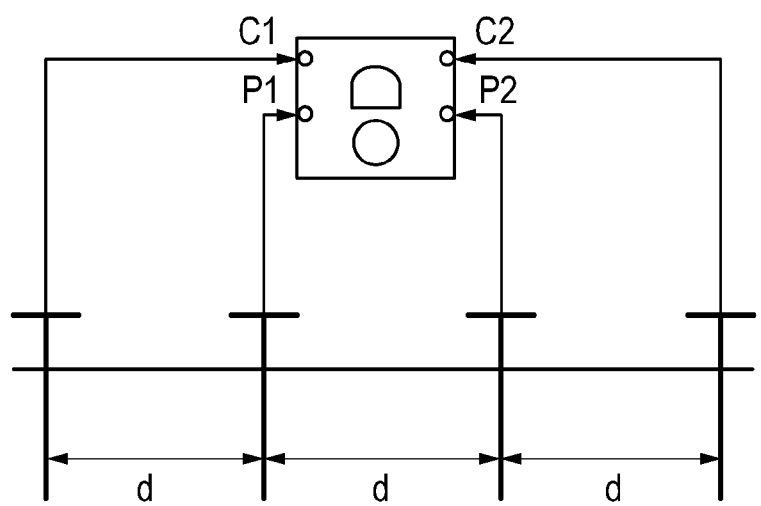

The data collection may include, but is not limited to, a Wenner four pin soil resistivity measurement. The soil resistivity at each transmission tower 104 (as shown in FIG. 1) may be measured using the Wenner four pin method in one location to various depths representing the depth of the structure, e.g. a depth of one, two and three feet. FIG. 3B is a schematic view of a data collection and associated calculations. Referring to FIG. 3B, d=spacing=depth (ft) and for determining resistance (R, ohms) one calculates resistivity (p, ohm-cm) where p=191.5*d*R.

The data collection may include, but is not limited to, electrochemical and physical measurements. The assessment protocol of the transmission towers 104 may use a combination of electrochemical and physical measurements that were used to determine the propensity of the environmental causes for corrosion. These data collection methods may include, but are not limited to, AC voltage measurements, DC voltage measurements, LPR corrosion rate measurement (to determine the relative corrosion rate of soil), soil pH, soil resistivity, soil chemistry, redox (oxidation-reduction) potential, coating thickness, degradation documentation, nondestructive testing or examination (which are commonly referred to as "NDE" examination) of a structure (e.g. tower, pipeline, etc.) and the like.

The AC voltage measurement may include a high voltage safety test which is first conducted to verify that the structure is safe to work near. An AC voltage test may then be made at each leg 126 of the transmission tower 104 (as shown in FIG. 1). The AC voltage test may be performed by placing a copper-copper sulfate reference electrode twelve to eighteen inches from the tower leg. The half cell may be connected to a Fluke multi-meter common terminal and the tower may be connected to a positive terminal of the voltmeter as shown in FIG. 3A. A fifteen volt maximum criterion may be used to determine if there is a shock hazard.

The DC voltage measurement may be performed at each leg 126 of the transmission tower 104 (as shown in FIG. 1) in the same manner as the AC measurements except the voltmeter may be set to measure DC voltage. The electrochemical potential of galvanized steel is expected to be more negative than −0.750 volts (CSE) when the galvanizing is new and intact and not adversely affected by high concentrations of carbonates and nitrates in the soil. These compounds may passivate the zinc and drive the electro-chemical potential in the positive direction. The electro-chemical potential of unprotected bare carbon steel in soils is expected to be −0.650 volts to −0.750 volts (CSE) when first exposed and will migrate in the positive direction over time as corrosion progresses. A potential of −0.550 volts (CSE) is considered a typical free corrosion potential of carbon steel that has experienced some corrosion. Carbon steel when bonded to copper may exhibit potentials that are in the range of −0.400 volts (CSE).

Figures 4A, 4B, 4C:
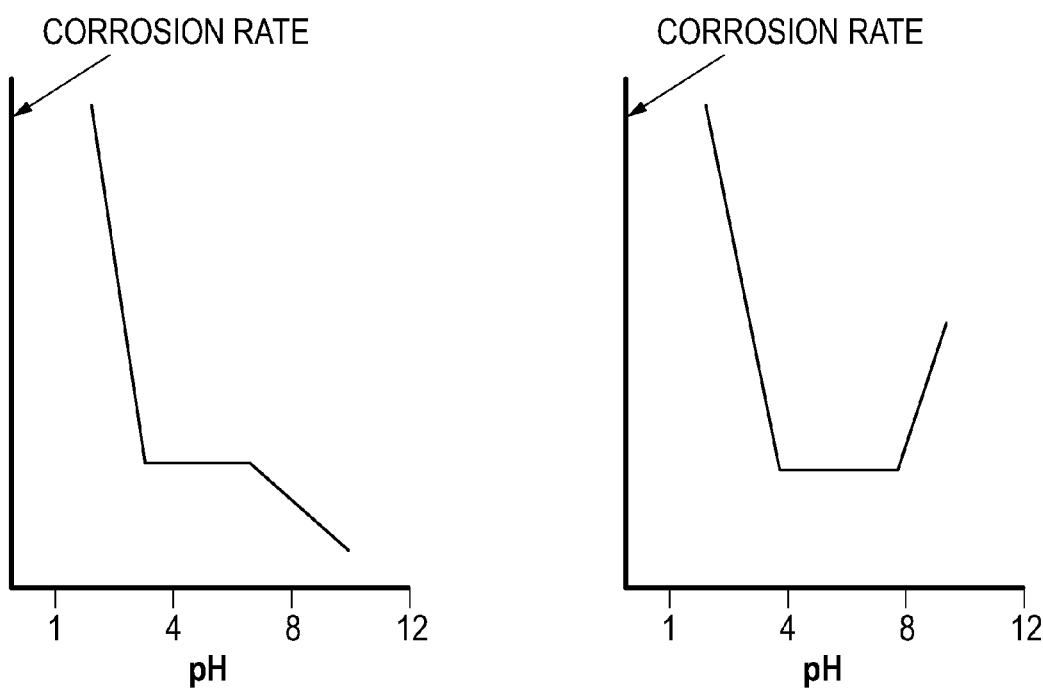
FIG. 4A depicts a general characterization of soil corrosivity based on soil resistivity measurements.
FIGS. 4B and 4C depict pH versus corrosion rate graphs for steel and zinc respectively.

Soil resistivity measurements may be taken for various depths below ground level to assess the potential corrosivity of the soil surrounding the buried portion of the structure. Soil resistivity is in the inverse of conductivity and may provide an indication of soil corrosivity. FIG. 4A depicts a general characterization of soil corrosivity based on soil resistivity measurements. The data shown in FIG. 4A indicates that there are areas of higher soil resistivity values that are typical of the elevated terrain and soil conditions.

The corrosion rate of a carbon steel probe installed into the soil at a distance of three feet from each tower leg was measured and recorded using a Linear Polarization Resistance (LPR) meter. Equation 2.1 below was used to calculate the corrosion rate from the measurements:

$$R_p = (\partial E / \partial I)_{i=0}$$

$$i_{corr} = (1/R_p)\beta_a\beta_c/2.303(\beta_a+\beta_c)$$

$$CR(mpy) = i_{corr} \times 129 \times WT/n \times d \quad \text{(Equation 1)}$$

The soil pH at each tower leg was measured and recorded using a Fluke multi-meter connected to a saturated copper-copper sulfate reference electrode (− negative terminal lead) and a antimony reference cell (+ terminal lead).

The soil pH is an indication of the degree of its acidity or alkalinity. pH is defined as the negative logarithm of the hydrogen ion concentration of the environment as depicted in the following equation:

$$ph = -\log[H]^+ \quad \text{(Equation 2)}$$

A pH of 7 is considered neutral and indicates that the number of hydrogen ions in solution is equal to the number of hydroxyl ions in solution. The relationship of pH to the impact of corrosion for steel and zinc is shown in FIGS. 4B and 4C.

A review of the data indicates an overall trend of the towers being in soils ranging from 2.6 to 9.7 with the average at 5.2. Generally the low pH of a soil indicates increased corrosivity for both the galvanizing and the steel. It should be noted that a single unit of pH change causes a factor of approximately 10 increase or decrease on corrosion rate.

The redox potential was measured and recorded for each tower. The redox potentials are an indication of the oxidation-reduction potential of the soil environment. They are typically used to determine the propensity of microbial activity in the soil that may contribute to microbiologically induced corrosion (MIC) and in particular, sulfate reducing bacterial induced corrosion. Values that are less than 150 millivolts indicate a moderate tendency of MIC while negative values indicate a severe tendency of MIC.

Coating thickness was measured and recorded using an electronic coating film thickness gauge to test the thickness of the zinc coating at two locations on each tower leg. One location was 12 inches above the ground level and the other was 12 inches below the ground level.

Although several data collection systems, methods and/or devices are described it should be appreciated that any suitable data collection systems, methods and/or devices may be used. During each of the data collection methods, the worker and/or the data collection tools may input the results of the data collection into the data input device 112 and/or the computer 124.

The data collection phase may determine any number of data elements for each of the transmission towers 104, the tower footings 128, and/or the legs 126. In one example up to sixteen data elements were collected to assist the prediction of the likelihood of corrosion and to measure the actual corrosion on the transmission towers 104. The data elements may include, but are not limited to, GPS coordinates, AC tower to soil potential, DC tower to soil potential, LPR corrosion rate measurement, visual corrosion pattern, section loss length, maximum pit depth, soil chemistry (chlorides, sulfates, passivation including carbonates bicarbonates and nitrates, antimony cell pH, redox potential, coating thickness 12" above soil, coating thickness 12" below the soil, soil resistivity, soil resistivity variation, soil type, topography, vegetation, photography, comments, electrochemical factor(s) (e.g. structure potential, structure potential variation, and corrosion rate), stray current interference factor(s), design factor(s) (e.g. type of structure and copper ground), visual corrosion factor(s) (e.g. general corrosion, section loss and pitting), cathodic protection factor(s) (e.g. applied cathodic protection and protection level) and the like. Several data elements are shown in FIG. 5. The data elements may be selected on the basis of their relevance to the likelihood of corrosion in the localized area of the individual towers and/or actual wall loss.

The collected data and/or the data elements for each of the transmission towers 104 surveyed may be sent to the infrastructure unit(s) 116 via the data input unit 108, the computer 124 used by the field worker 108, and/or entered by the worker 118 at the service company 120. The worker 118 at the service company 120 may input the data into the infrastructure unit 116 from data collected in a data collection sheet 600 as shown in FIG. 6.

Figure 7:
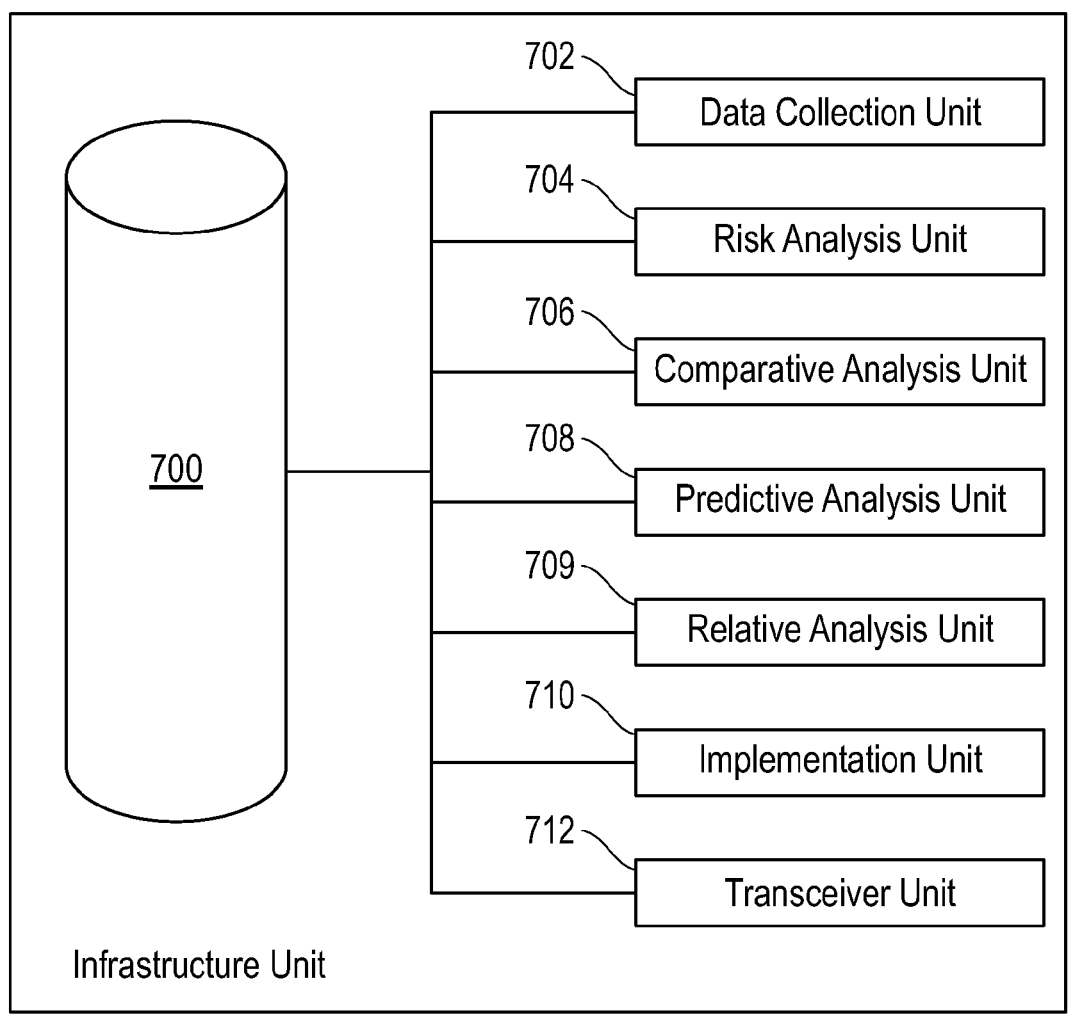
FIG. 7 depicts a block diagram of an infrastructure unit of the infrastructure analysis system.

FIG. 7 depicts a block diagram of the infrastructure unit 116 according to an embodiment. The infrastructure unit 116 may include a storage device 700, a data collection unit 702, a risk analysis unit 704, a comparative analysis unit 706, a predictive analysis unit 708, an implementation unit 710 and a transceiver unit 712. The storage unit 700 may be any suitable storage device for storing data. The transceiver unit 712 may be any suitable device configured to send and/or receive data to the infrastructure unit 116. The infrastructure unit 116 may be totally or partially located in the one or more data collection tools 110, the one or more data input devices 116, the computers 124 and/or the network 114.

The data collection unit 702 may collect all of the data including, but not limited to, input by the field worker 108 into the one or more data collection tools 110 and/or the computer 124. The data collection unit 702 may then identify important data elements from the collected data. The data unit 702 may then organize, store, categorize, and manipulate the collected data per the needs of the project. The data collection unit 702 may further keep historical data regarding any of the collected data, data elements, and/or power infrastructure 102 as the data is collected.

The risk analysis unit 704 may receive information from the data collection unit 702 to determine risk, or risk factors, in the power infrastructure 102. The risk analysis unit may have a transmission corrosion analysis tool (or "TCAT™"), tower version, and a graphical information system (or "GIS"). The risk analysis unit 704 may evaluate, manipulate, analyze and characterize the data from the data collection unit 702 in order to determine risks, damage, and the like of the power infrastructure 102 that has been observed. The risk analysis unit 704 may analyze the data and classify the degradation on the power structure including, but not limited to, the individual legs, towers, and circuits. The risk analysis unit 704 may correlate the degradation classification with the risk scores and perform an overall assessment of the power infrastructure 102 including, but not limited to, the legs 126, the transmission towers 104, the footings 128, and the circuits.

Figure 8A:
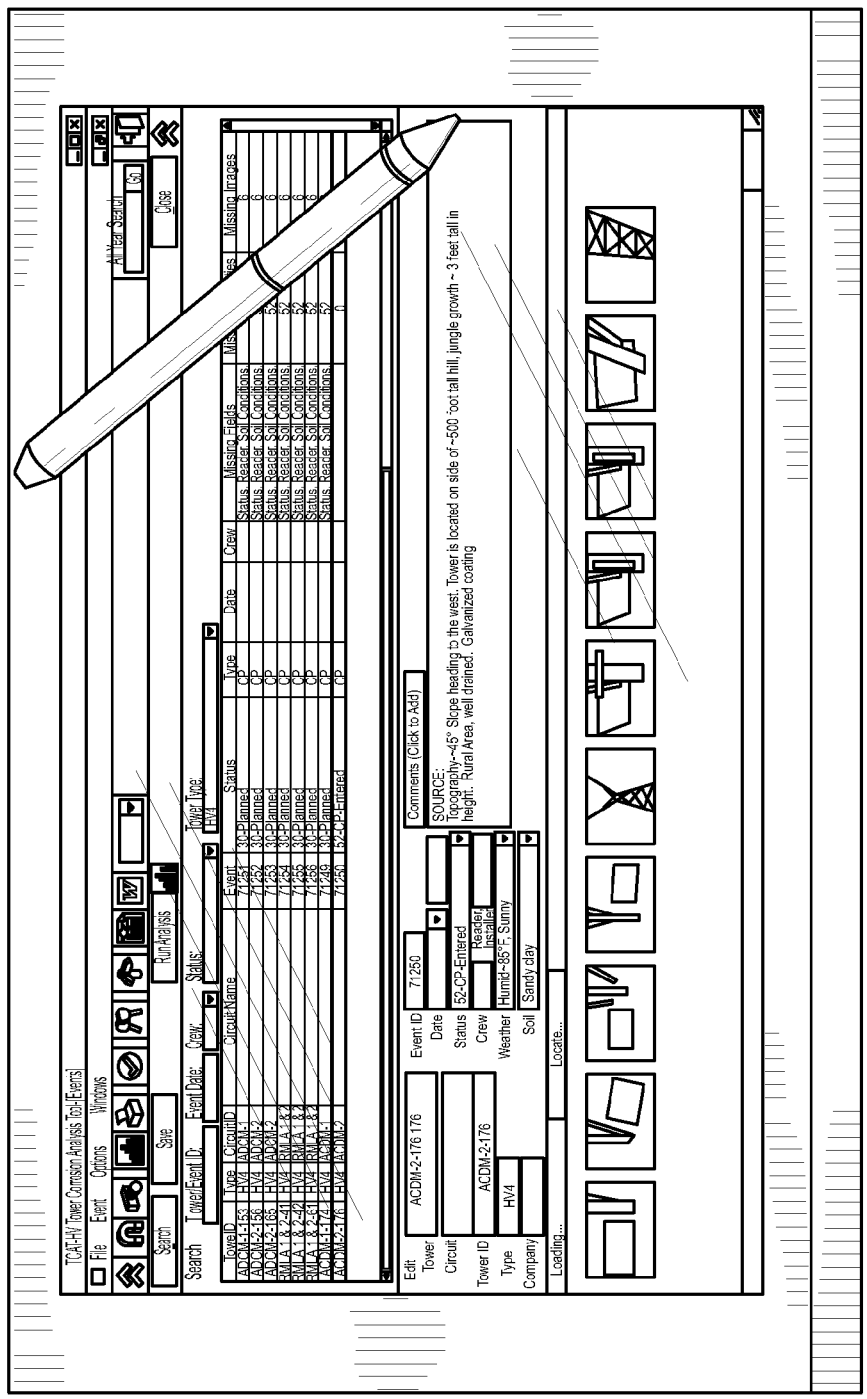
Figure 8B:
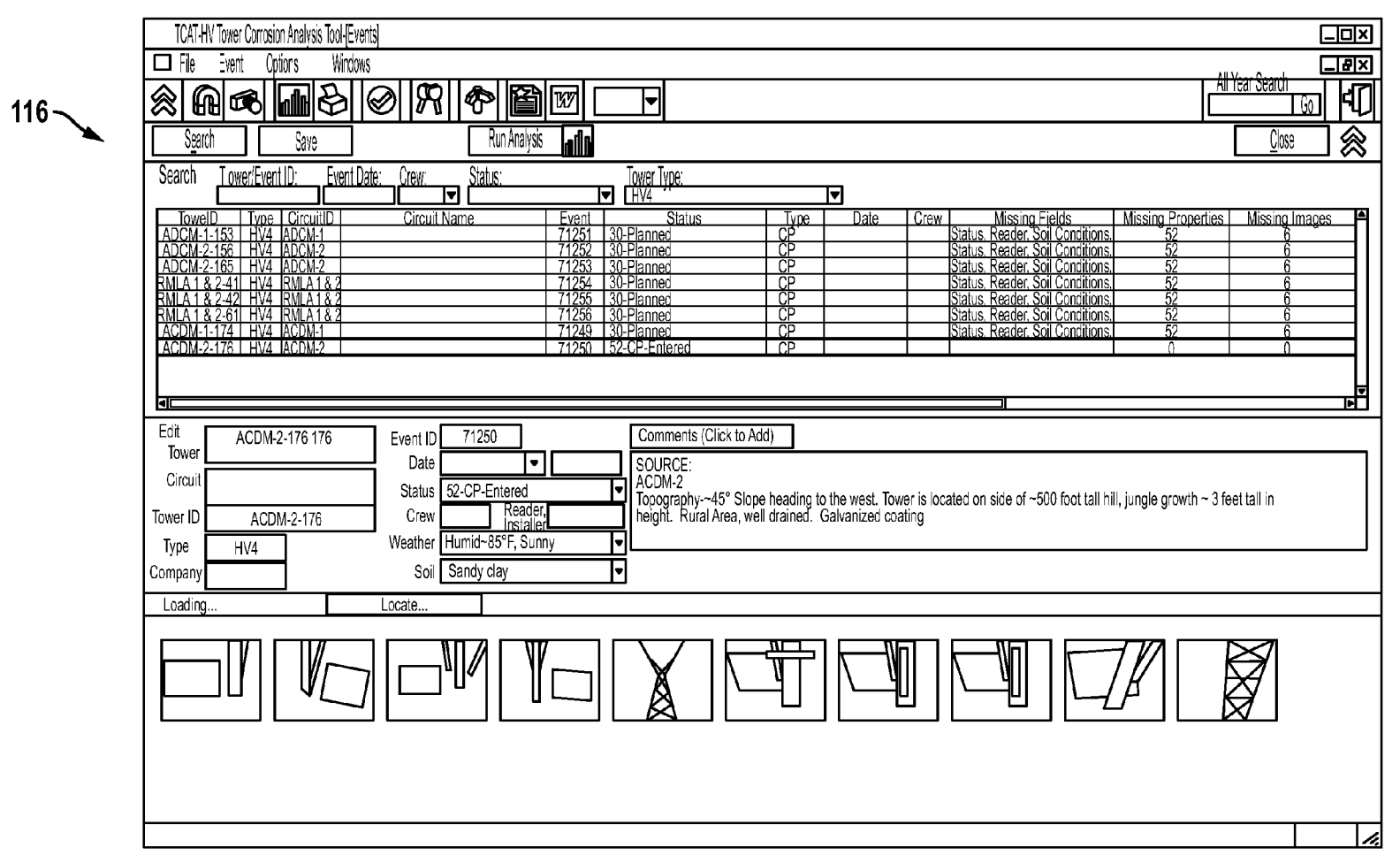

The TCAT™ allows the workers to acquire, store and manage tower related data and timely performance of risk ranking calculations. This may allow for quick identification of towers with the highest risk of degradation and timely direction of remediation crews to those high risk transmission towers 104. FIGS. 8A and 8B depict a portion of a visual display of the TCAT™. The TCAT™ model may use an algorithm developed according to one having ordinary skill in the art in corrosion science and field deployable electrochemical measurements. By way of example this algorithm integrates sixteen data elements, for example sixteen electrochemical, chemical and physical measurements for the power infrastructure 102, such as the transmission towers 104, the legs 126, and the like. The algorithm may determine or infer the relative likelihood of corrosion of that power infrastructure. To continually improve the performance of the model, direct information or information used to infer conditions may be integrated, for example, the subsurface direct examination condition data of the footings may be inputted with direct observations. This allows the TCAT™ model and the assessment team performance to improve in real time as data is collected for a specific assessment project, or implementation project. The TCAT™ model and/or the risk analysis unit 702 may characterize soil characteristics, electrochemical factors, electrical interferences, design, cathodic protection, topography, and the like for the power infrastructure 102.

The risk analysis unit 702 and/or the TCAT™ may provide the description of the degradation classifications and the corresponding total risk score for those classifications based on the data obtained from the data collection phase. The total risk score may be created by integrating the results of the subsurface direct examination of the tower footings/anchors 128 with corresponding risk scores. During the course of the data collection, the project, and/or the implementation project, correlations may be recognized between the risk scores and the ranges of metal loss in the power infrastructure 102. FIG. 9 depicts a correlation of risk score and degradation classification created by the risk analysis unit 702. FIGS. 10A-10C 1000 show displays of various risk scores sorted by overall tower risk, highest leg risk or highest risk in each of the two circuits. The displays allow the implementation team to quickly review and identify the high risk portions of the power structure 102.

Figure 10A:
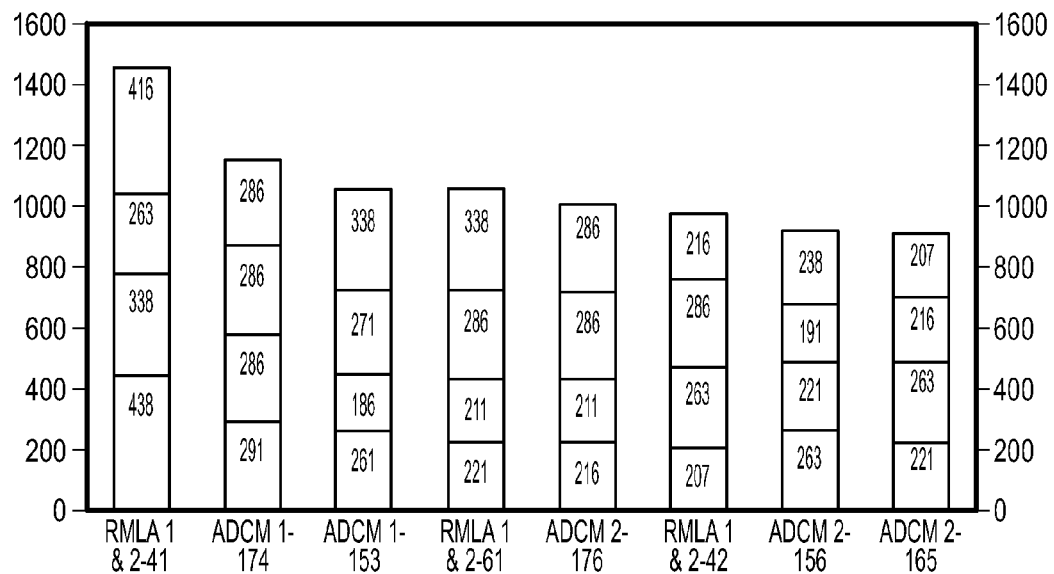
FIGS. 10A-10C show displays of various risk scores created by the infrastructure unit.
Figure 10B:
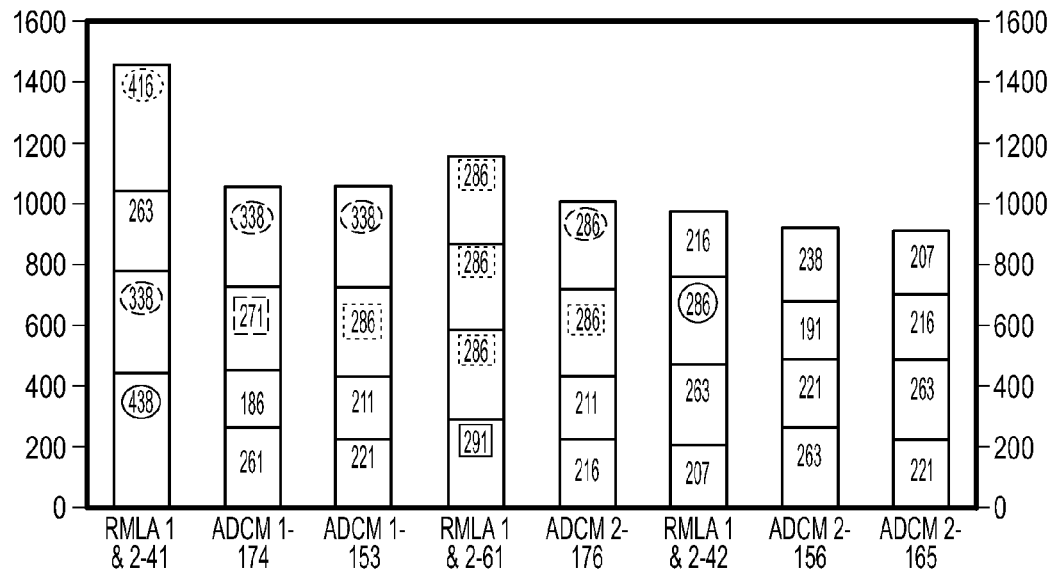
Figure 10C:
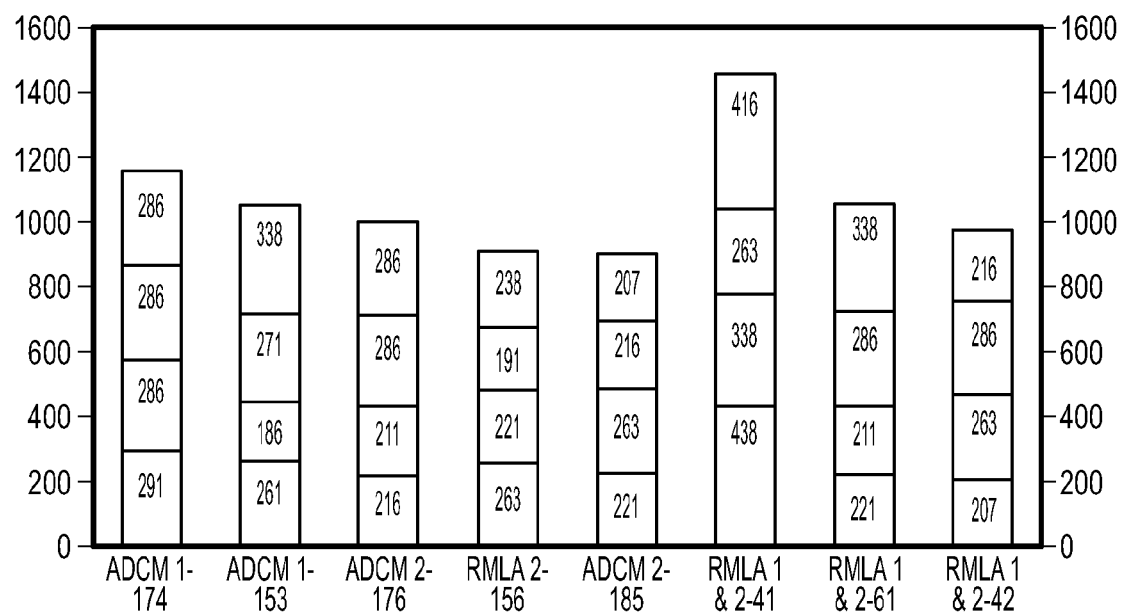
Figure 10D:
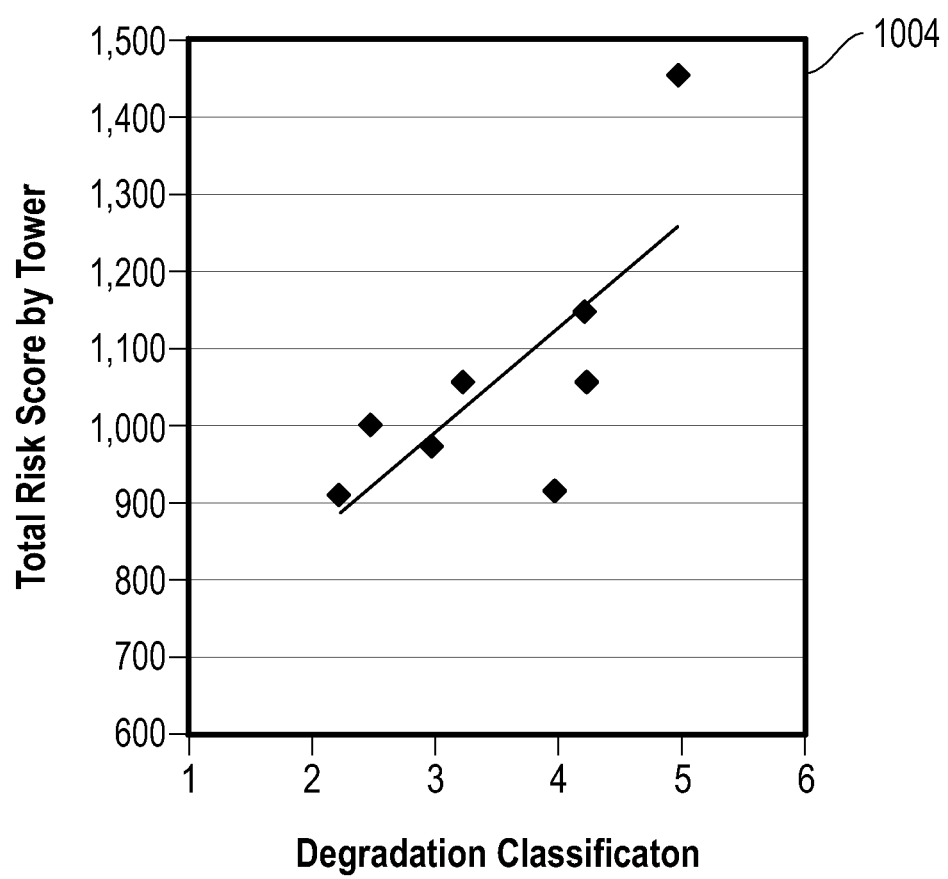
FIG. 10D depicts a table showing a total risk score for a transmission tower.

The TCAT™ corrosion prediction model and/or the risk analysis unit 702 may provide a relative ranking of the severity of degradation of the transmission towers 104 (as shown in FIG. 1). FIG. 10D depicts a table 1004 showing a total risk score for a transmission tower. The total risk score generally increased with increasing levels of degradation.

The risk analysis unit 702 may determine the degree of degradation for each transmission tower 104, for example in the legs 126. FIG. 11 depicts a table 1100 listing of photos taken at the power infrastructure 102 of amounts of degradation in the legs 126. The table 1100 may also provide a listing of photos of the degradation of the tower footing 128.

The comparative analysis unit 706 (as shown in FIG. 7) may compare data collected, the data elements, the TCAT™ models, the risk models, for each of the portions of the power infrastructure 102. For example, the comparative analysis unit 706 may compare the different transmission towers 104 in the power infrastructure 102. The comparative analysis unit 706 may determine varying degrees of risk, performance, and/or degradation for each of the transmission towers 104.

The predictive analysis unit 708 may take the data from the data collection unit 702, the risk analysis unit 704 and the comparative analysis unit 706 in order to predict the future performance of the portions of the infrastructure 102 that have been modeled. This may allow the implementation team to determine a maintenance and/or remediation schedule for the power infrastructure. The predictive analysis unit 708 may forecast degradation of the portions of the power infrastructure 102. For example, a corrosion based life cycle analysis may be developed using the degradation classification criteria in FIG. 4D. This life cycle analysis may be enhanced by integrating structural analysis and/or consequence of failure data with the risk analysis unit 704. These life cycle analyses will allow the prioritization of the power infrastructure including, but not limited to, the footings 128, the transmission towers 102, the legs 126, and/or the circuits. This may allow the implementation team to develop a multi-year refurbishment plan for the power infrastructure 102.

The relative analysis unit 709 may take the data from the data collection unit 702, the risk analysis unit 704, the comparative analysis unit 706 and the predictive analysis unit 708 in order to predict the present and future condition of portions of the power infrastructure 102, and/or other infrastructure systems, for which no, or little, data has been collected. Based on the known data from the measured power infrastructure 102, the relative analysis unit 709 may determine with a high degree of probability the status and future status of the power infrastructure 102. This may allow the implementation team to determine a maintenance and/or remediation schedule for the power infrastructure that has not yet been measured and/or observed. This may save time and money of the work crews.

The implementation unit 710 may take the data from the data collection unit 702, the risk analysis unit 704, the comparative analysis unit 706, the predictive analysis unit 708, and the relative analysis unit 709 in order to create an implementation plan. The implementation plan may include, but is not limited to, maintenance plans and schedules, remediation plans and schedules, and construction plans and schedules, corrosion mitigation plans and schedules for any of the components of the power infrastructure 102.

The degree of degradation of the power infrastructure 102 (as shown in FIG. 1) such as the footings 128 may be distributed over a wide range of degradation ranging from very little to 100% metal loss on some components. The infrastructure unit 116 may perform life cycle analysis on the power infrastructure 102. The life cycle analysis may provide a prioritization schedule of when to remediate each of the transmission towers 104. Therefore, the infrastructure unit 116 may develop a multi-year, cost efficient remediation plan, repair plan, maintenance plan and/or construction plan on a system wide basis. The projected degradation determined by the infrastructure unit 116 may assist in the timing of remediation and repair of the power infrastructure 102 thereby extending the life of the equipment and saving money for the owner of the power infrastructure.

In one example, estimated wall losses from the visual assessments by the field worker 108 were used as a baseline. Corrosion rates were estimated by the infrastructure unit 116, for example from the electrochemical measurements made at the transmission towers 104. With the corrosion rates, projections of degradation classifications were made for three, five and ten years into the future. FIG. 12 depicts a table 1200 generated by the infrastructure unit 116 that depicts the projected degradation classification for each transmission tower 104 (as shown in FIG. 1) that may be assessed. It is estimated that the yellow, orange and red degradation levels may result in a structural compromise of the transmission tower 104. The infrastructure unit 116 may determine which transmission tower 104 needs mitigation measures based on the table 1200. The mitigating measures may prevent the transmission tower 104 from experiencing a higher classification level of degradation.

Figure 13A:
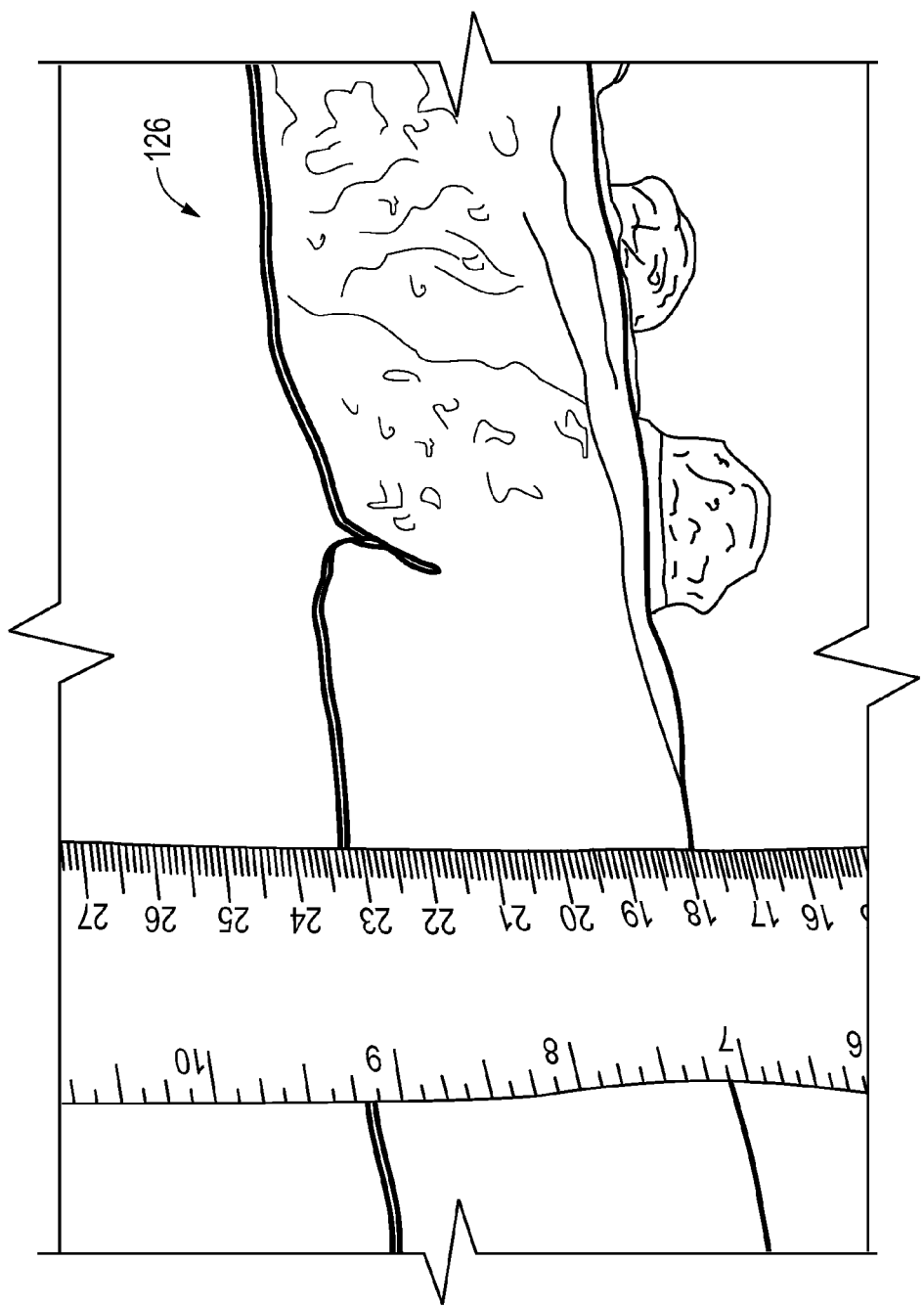
Figure 13B:
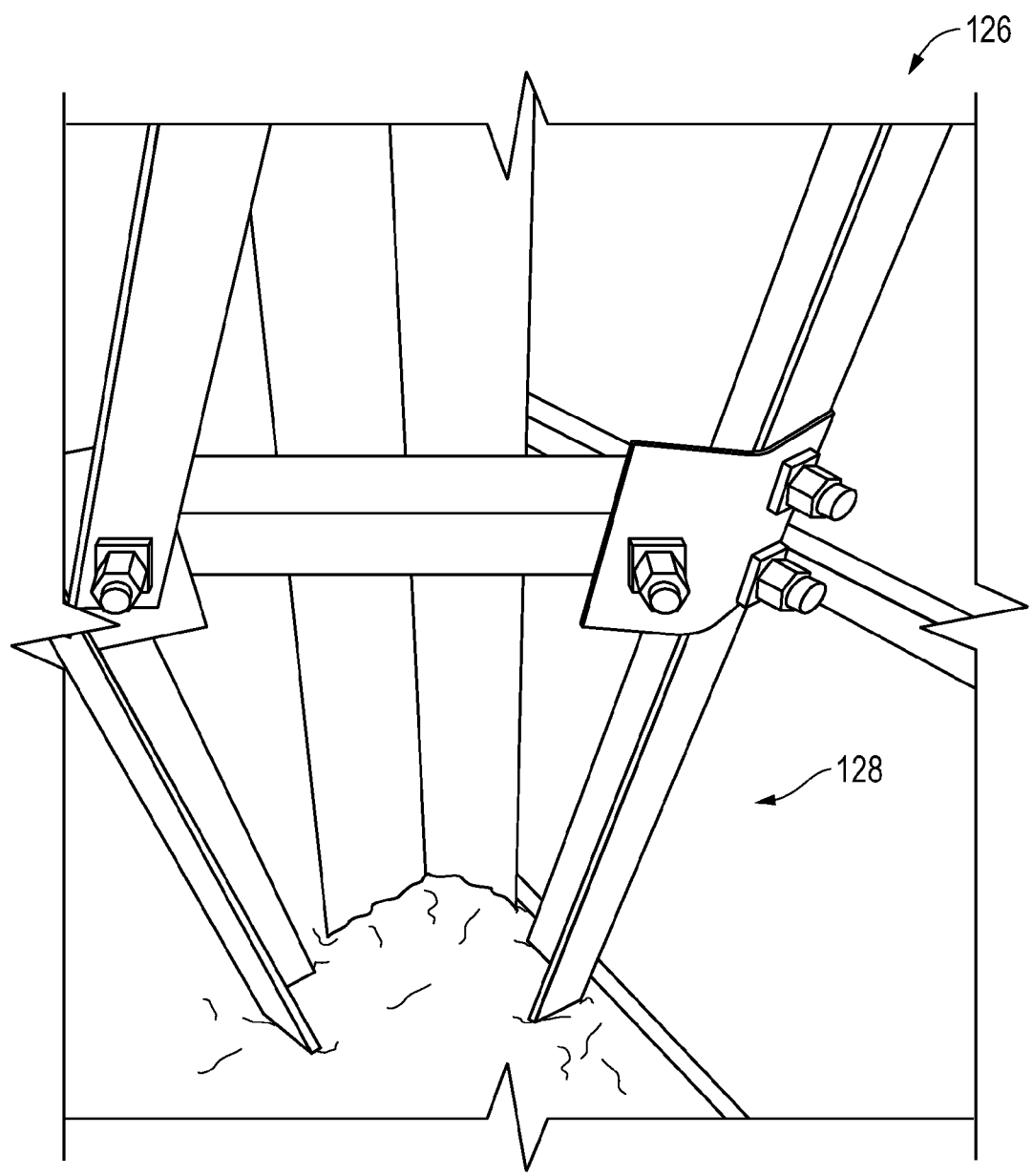
Figure 13D:
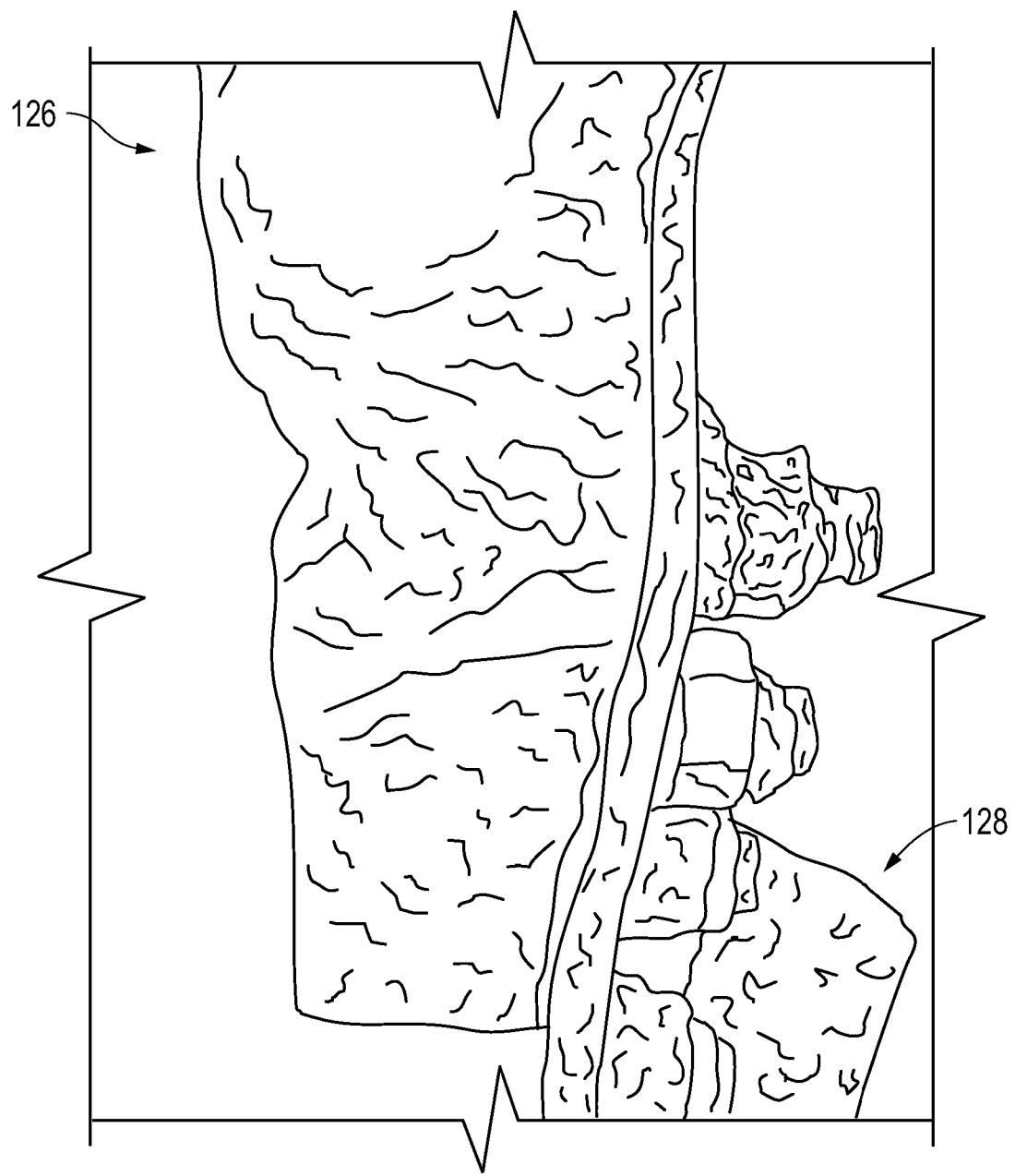

In one example of an operation performed, fifty percent of the footings 128 (as shown in FIG. 1) that were assessed had a degradation category of 4 or greater. This is indicative of metal loss between thirty to one-hundred percent on some components of the footings 128. The degradation tended to be more severe at the air/soil interface of the footings 128. At the air/soil interface the edge of the angle iron had the greatest corrosion as the result of the zinc coating being thinner on the edges and the edges being more susceptible to mechanical damage. For example on leg B of the tower ADCM-2-156 portions of an angle iron support had completely corroded away and the remaining ligament was cracked as shown in FIG. 13A.

Remediation may involve excavation of each affected tower leg to be remediated to a depth of three feet, cleaning of the exposed steel grillage to a SSPC Cleaning Standard, application of a protective coating or replacement of the degraded tower component. Remediation may also include the auger and attachment of one (1) or more High Potential Magnesium Anodes to each tower leg or other buried component, Photographic documentation, and commissioning performance testing and documentation.

FIGS. 13A-13D depict photos of portions of the infrastructure system. For further reference to an existing infrastructure system, please see U.S. patent application Nos. 61/482,538 and 61/598,192, the benefit of which are herein claimed, and the disclosures of which are hereby incorporated by reference.

Figure 14:
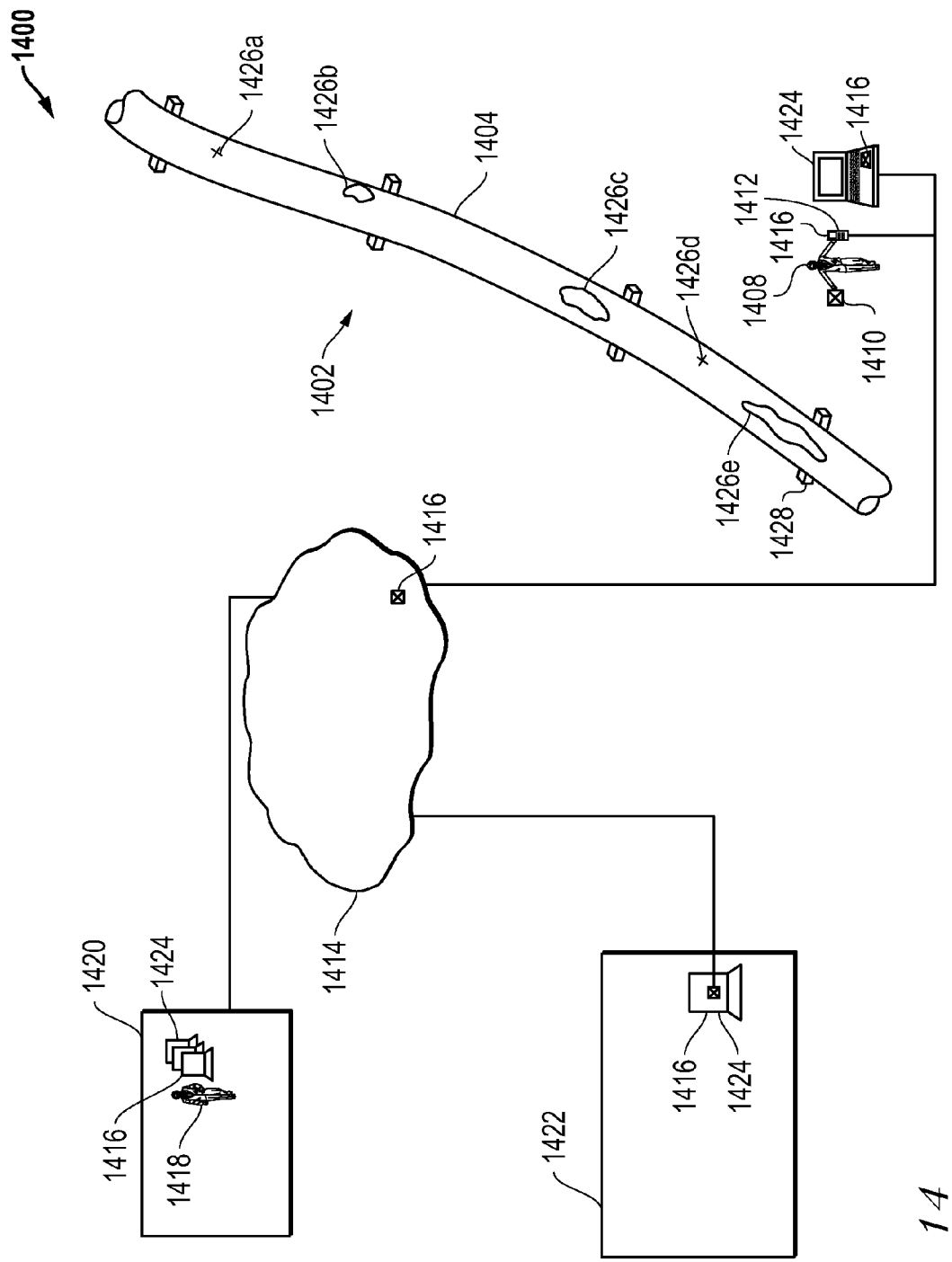
FIG. 14 depicts a schematic view of a pipeline analysis system.

FIG. 14 depicts a schematic view of a pipeline analysis system 1400. The analysis system 1400 may be for analyzing conditions and/or damage to a pipelines and/or pipeline infrastructure 1402. As shown the pipeline infrastructure 1402 is a pipeline 1404 for transporting gases or fluids there through. The pipeline analysis system 1400 may have the pipeline infrastructure 1402, one or more field workers 1408, one or more data collection tools 1410, one or more data input devices 1412, a communication network 1414 and a pipeline infrastructure unit 1416. In addition, the pipeline analysis system 1400 may have one or more analysis workers 1418 at a service company 1420. The service company 1420 may be hired to perform analysis, maintenance, remediation, and/or construction on the pipeline infrastructure 1402. Further, the pipeline analysis system 1400 may communicate with a client company 1422. The service company 1420 and/or the client company 1422 may have any number of computers 1424 which may have the pipeline infrastructure unit 1416 therein. In addition to, or as an alternative to, the one or more data input devices 1412, the field worker may have a computer 1424.

The pipeline infrastructure 1402 may have the pipeline 1404 with one or more damaged portions 1426a-e (or greater). In addition, the pipeline infrastructure 1402 may have any suitable devices or equipment for supporting the transportation of gases or fluids in the pipeline 1404 including, but not limited to, pipe supports 1428, compressor stations (not shown), pumps (not shown), valves, and the like.

The damaged portions 1426 of the pipeline 1404 may be due to corrosion of the pipeline 1404. In addition, the damaged portions 1426 may be caused by any suitable factors including, but not limited to, weather, ph of soil, cathodic corrosion, biological corrosion 1404 and the like. In addition, the damage portion may be structural damage due to installation, impact, vandalism, and the like.

The field worker 1408 may be any suitable worker (such as a technician or an engineer) that is sent to the pipeline infrastructure 1402 to collect data during a data collection phase of the project. The field worker 1408 may input the collected data directly into the one or more data input devices 1412 and/or the computer 1424 as the data is collected in the field. The one or more data collection tools 1410 may communicate directly with the one or more data input devices 1412 and/or the computer 1424 or the field worker 1408 may input the collected data manually. As the data is collected, the one or more data input devices 1412 and/or the computer 1424 may send the data to the pipeline infrastructure unit(s) 1416 located about the pipeline analysis system 1400. The field worker 1408 may collect data for the pipeline 1404 as the field worker 1408 travels along the pipeline 1404. Further, the field worker 1408 may collect data from only a select section of the pipeline 1404 and then use the pipeline analysis system 1400 to predict the conditions along the pipeline 1404 and formulate a project plan, or implementation plan.

The one or more data collection tools 1410 may be any suitable device(s) for measuring conditions about the pipeline infrastructure 1402. In an embodiment, the field worker 1408 may use a caliper to measure the corrosion at the damaged portions 1426. The caliper may be any suitable caliper including but not limited to a digital caliper. Further, the data collection tools 1410 may be any suitable tools for collecting data concerning the damage and contributing factors including, but not limited to, a laser scanner, acoustic tools, cameras, GPS devices, surveying equipment, soil testers (such as pH, resistivity or redox), structure potentials as referenced to a copper-copper-sulfate reference cell, coating condition, water pH the field workers experience, pressure monitors, flow meters, a pipeline pig, a handheld computer with one or more data input features, data collection tools described herein, and the like.

The communication network 1414 allows for communication about the pipeline analysis system 1400 and may be any suitable network including those described herein.

The field worker 1408 may collect data from all, or portions of, the pipeline infrastructure 1402 during a data gathering phase of the project. During the data gathering phase the field worker 1408 may used the data collection tools 1410 and/or observation at the pipeline infrastructure 1402. The data collection may take place during routine pipeline surveys including, but not limited to, annual surveys. Further, the data collection may take place due to the identification of a specific problem along the pipeline including, but not limited to, a leaking pipeline, a corroded portion of the pipeline and the like.

The data collection may include identifying the damaged portions 1426a-e. After identification of a damaged area, the field worker 1408 may perform a more thorough investigation of the damage. For example, the field worker 1408 may determine both externally and internally the size of the corroded area, the depth of the corrosion in the pipe, the wall thickness erosion in the pipe, the soil type, soil resistivity, pipe-to-soil potentials, the material the pipeline is constructed with, the type thickness and condition of coating on the pipeline, coating damage, recoating data, defect size and/or location, the paint on the pipeline, paint damage, weld type and condition, magnetic particle analysis for crack identification, pH content, mapping of damaged areas, defect remaining strength analysis, corrosion product analysis, photos or digital imaging, dimensions of excavated areas, site sketches, depth of cover, global positioning, and the like. Further, a pig, or pipe pig, or digital pig may collect data regarding the condition of the pipeline as the pig travels through the pipeline.

The collected data may be automatically, and/or manually input into the one or more data input devices 1412 and/or the computer 1424. The one or more data input devices 1412 may be any suitable data input devices including, but not limited to, a tablet computer, a personal digital assistant, a smart phone, a laptop, a desktop, any suitable data input device described herein and the like.

Figure 15:
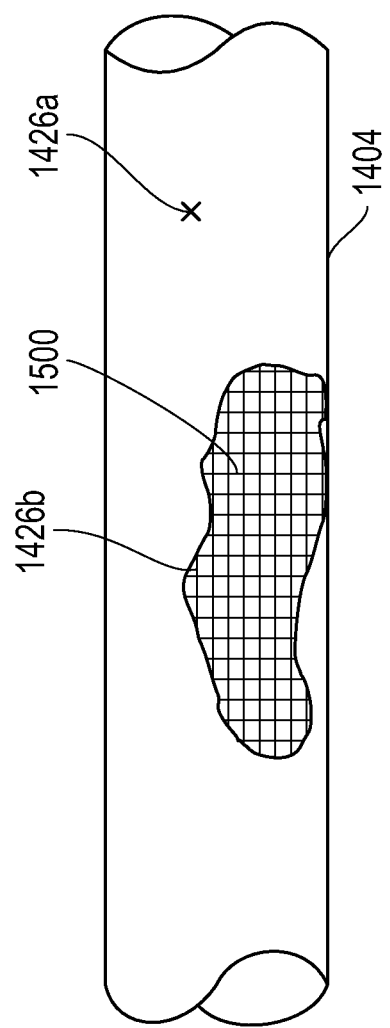
FIG. 15 depicts portion of a pipeline with one or more damaged sections.

FIG. 15 depicts two damaged portions 1426a and 1426b in an example. As shown, the damaged portion 1426a may be a very small corroded portion of the pipeline. The field worker 1408 may collect data regarding this damaged portion 1426a and provide a location on the pipeline 1404 to the pipeline infrastructure unit 1416 by any suitable method described herein. The damaged portion 1426b may be a larger damaged area that requires more detailed analysis, or mapping of the corrosion. As shown, a corrosion grid 1500 may be drawn on the pipeline 1404. The data collection tools 1410 may map the specific conditions of the corrosion along the entire corrosion grid 1500. The corrosion grid 1500 may be drawn on the pipeline 1404 by the field worker 1408, or may be put on the pipeline 1404 via one of the data collection tools 1410. Once the data is collected a mitigation plan is devised and implemented in order to ensure that there is not pipeline failures as will be described in more detail below.

The collected data and/or the data elements for each of the pipelines 1404 surveyed may be sent to the pipeline infrastructure unit(s) 1416 via the data collection tools 1410, the data input devices 1412, the computer 1424 used by the field worker 1408, and/or entered by the worker 1408 at the service company 1420. The worker 1418 at the service company 1420 may input the data into the pipeline infrastructure unit 1416 from data collected in a data collection phase.

Figure 16:
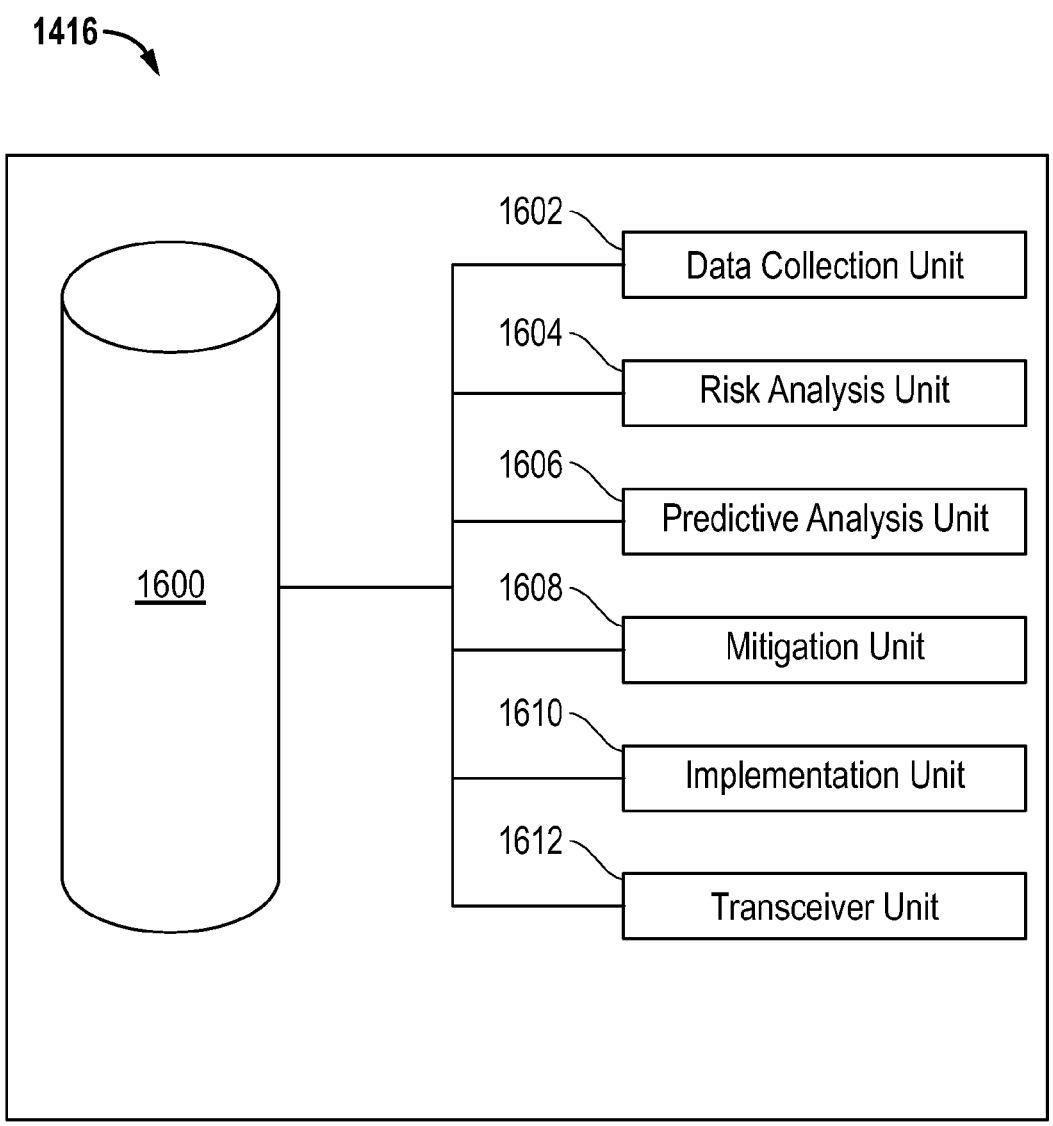
FIG. 16 depicts a pipeline infrastructure unit according to an embodiment.
Figure 17G:
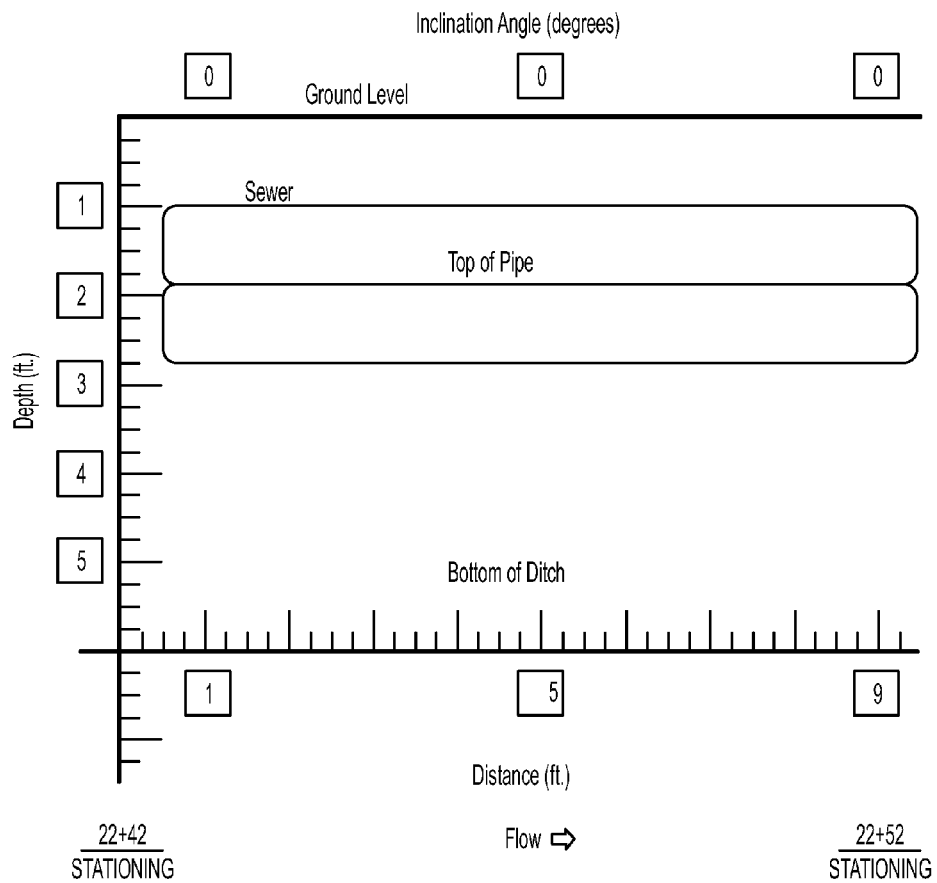
Figure 17H:
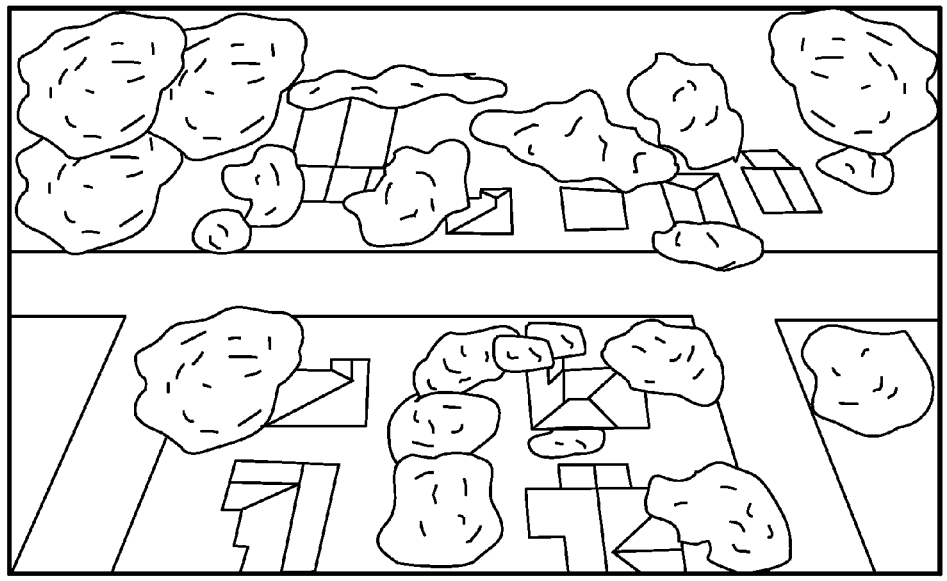

FIG. 16 depicts a block diagram of the pipeline infrastructure unit 1416 according to an embodiment. The pipeline infrastructure unit 1416 may include a storage device 1600, a data collection unit 1602, a risk analysis unit 1604, a predictive analysis unit 1606, a mitigation unit 1608, an implementation unit 1610, and/or a transceiver unit 1612. The storage device 1600 may be any suitable storage device for storing data. The transceiver unit 1612 may be any suitable device configured to send and/or receive data to the pipeline infrastructure unit 1416. The pipeline infrastructure unit 1416 may be totally or partially located in the one or more data collection tools 1410, the one or more data input devices 1412, the computers 1424, at the service company 1420, client company 1422 and/or with the field worker 1408, and/or the network 1414.

Figure 18A:
Figure 18B:
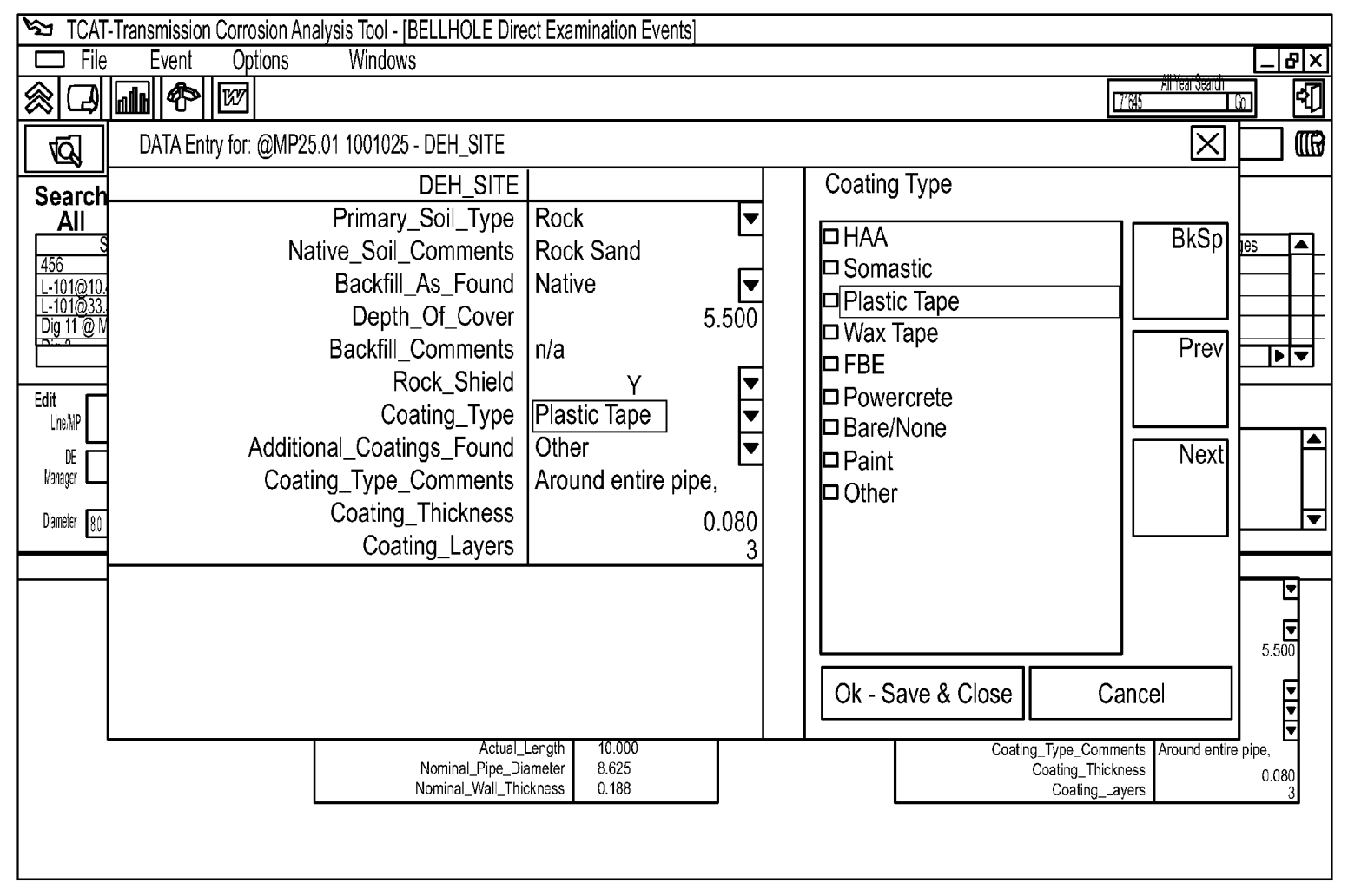
Figure 18C:
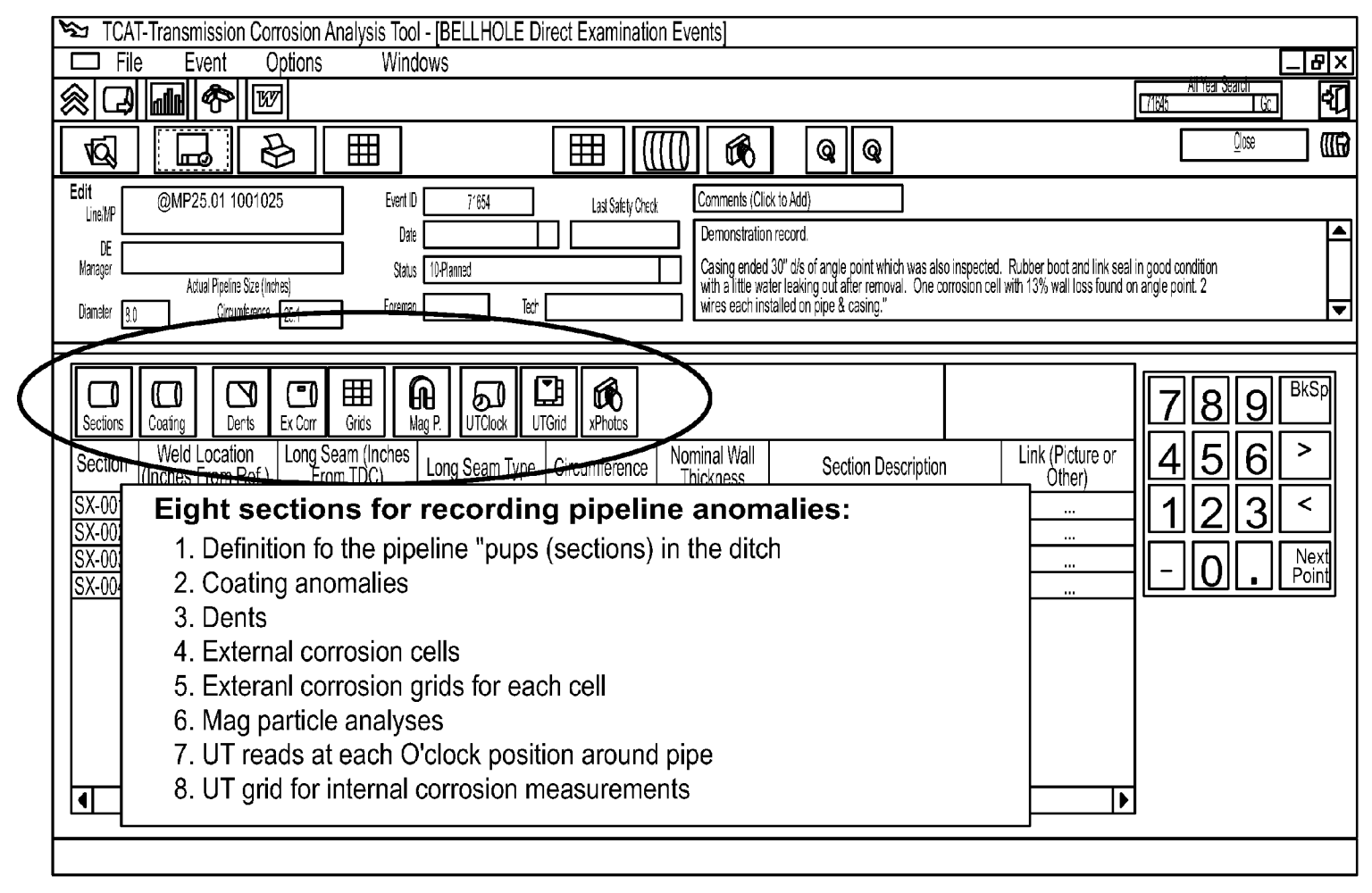
Figure 18D:
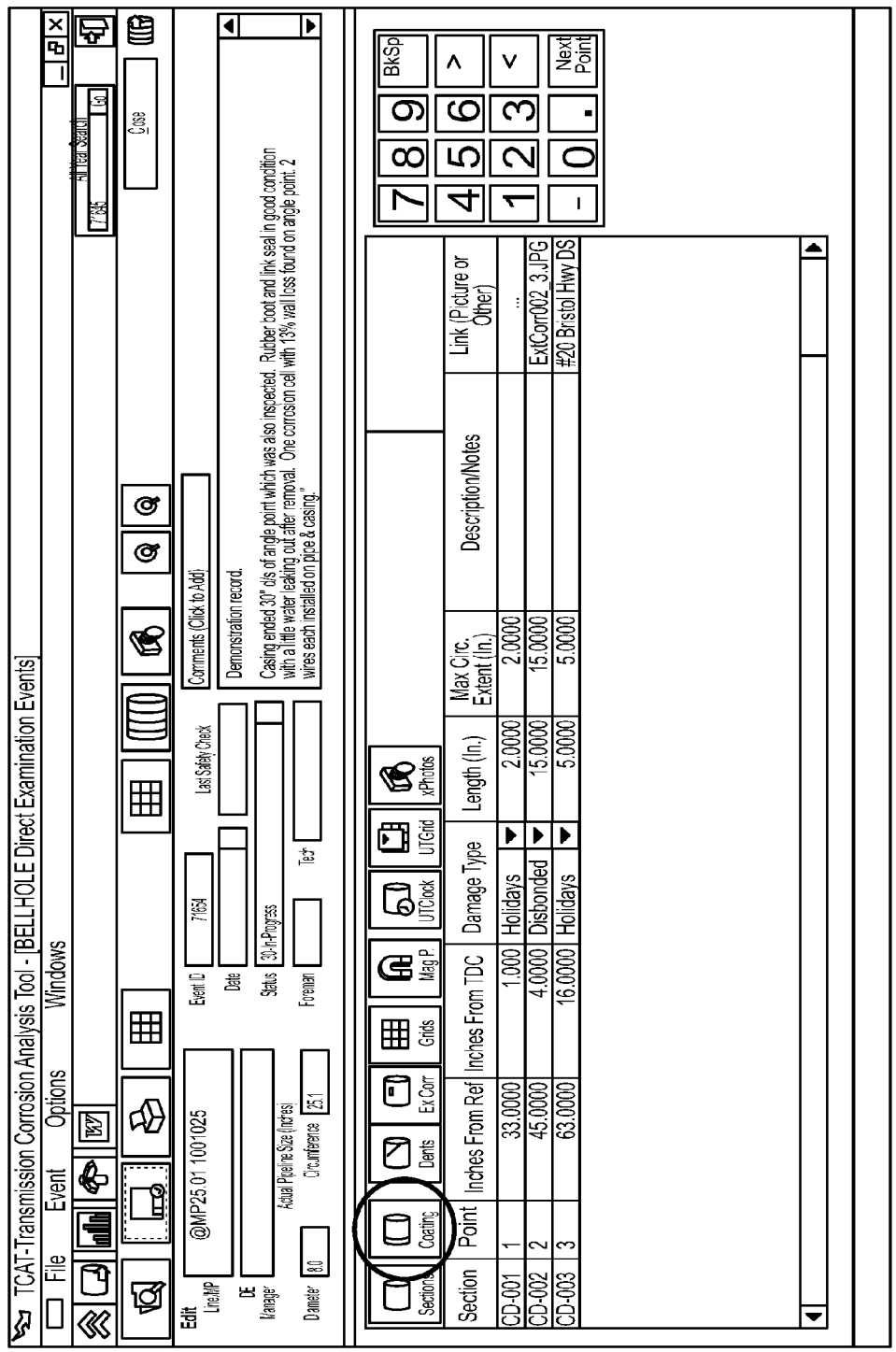
Figure 18E:
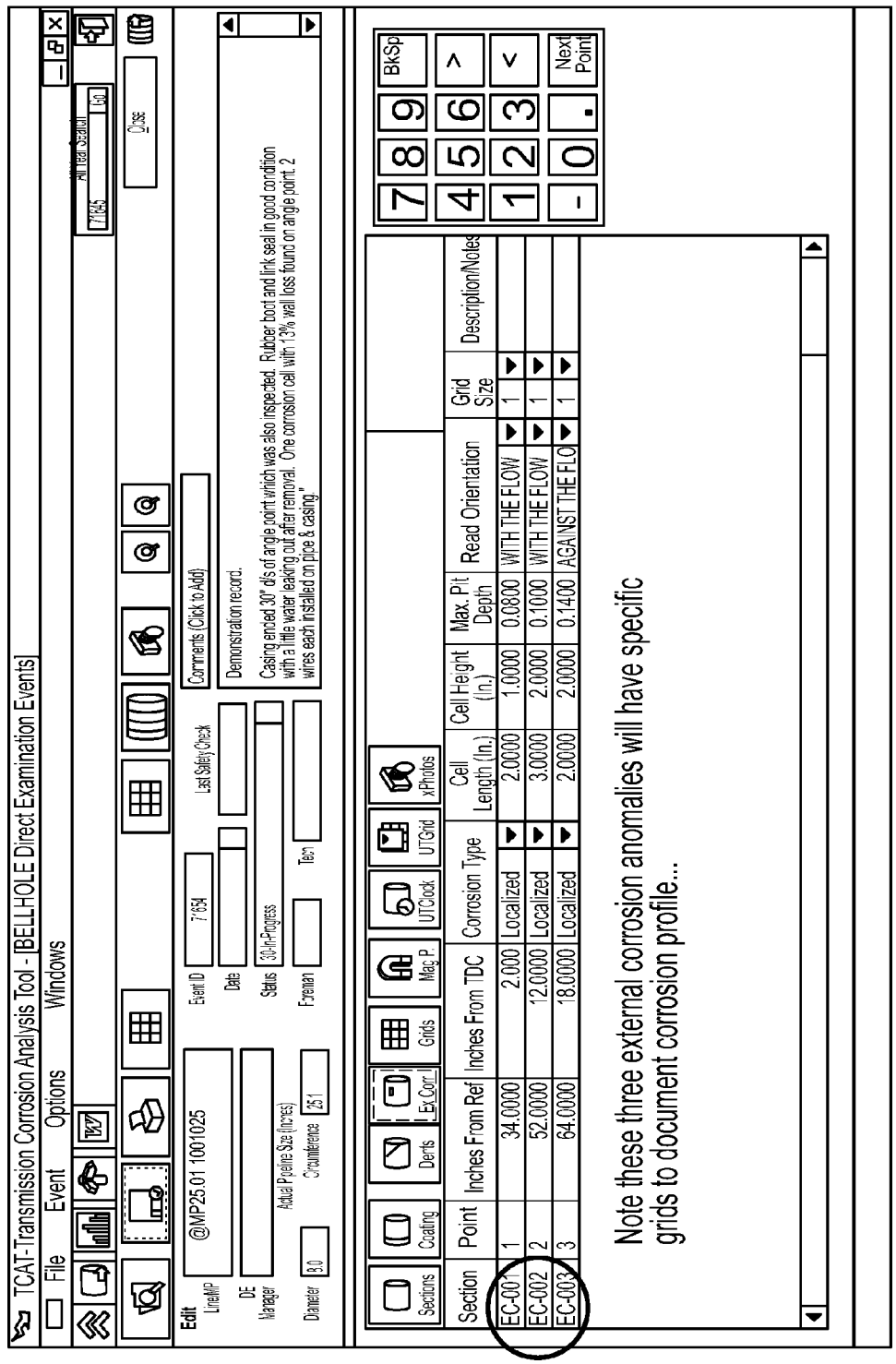
Figure 18F:
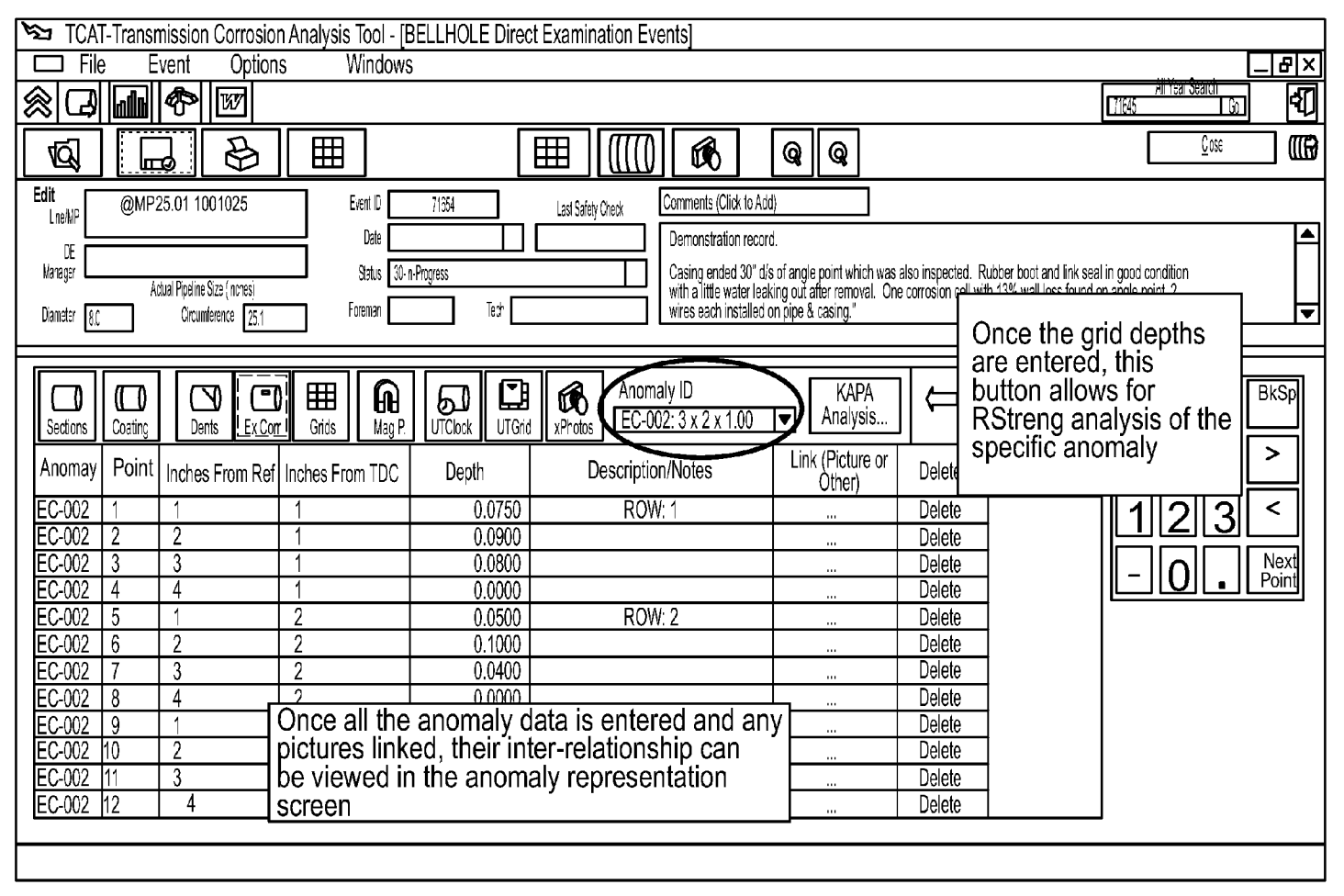
Figure 18G:
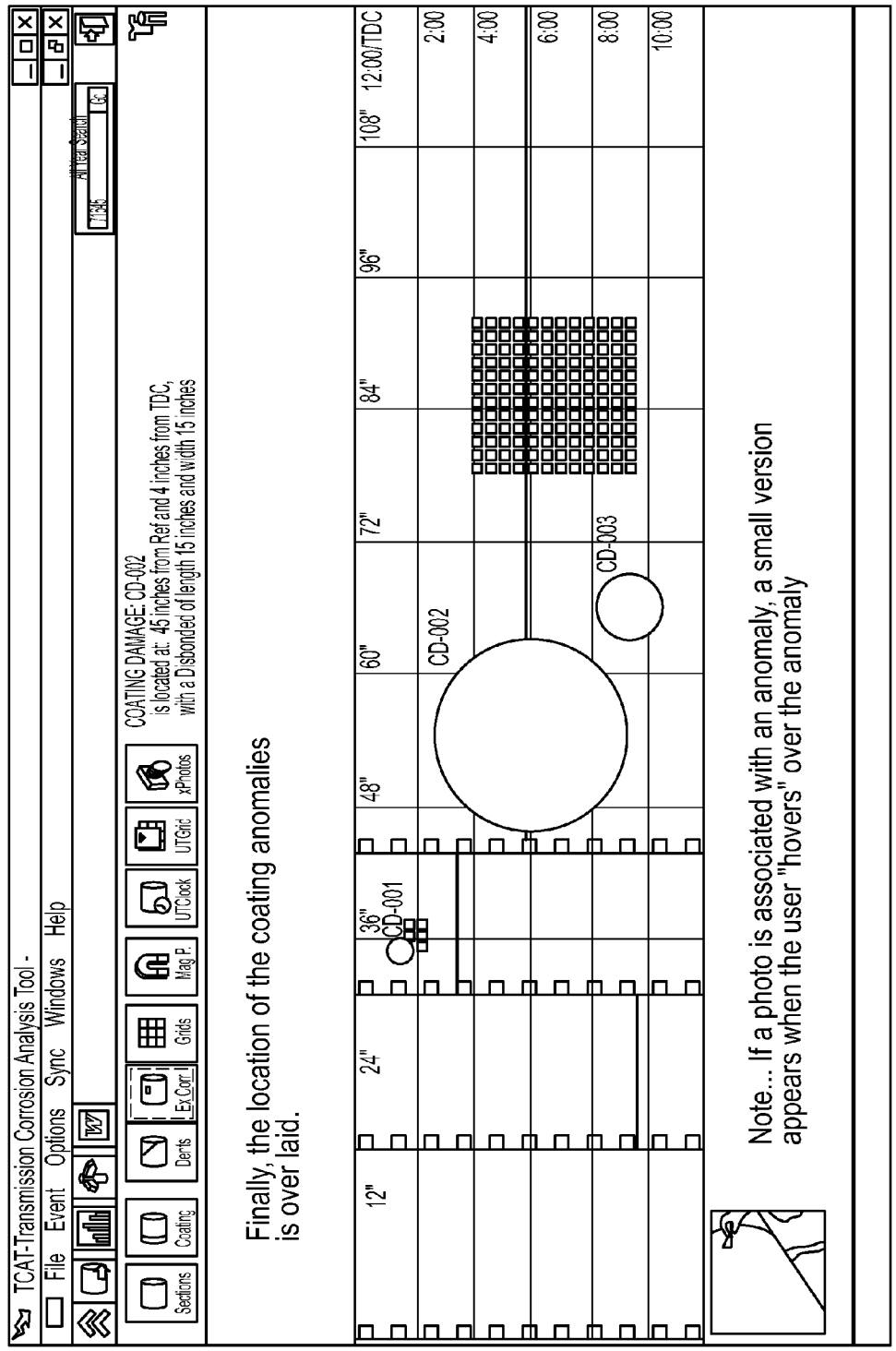
Figure 18H:
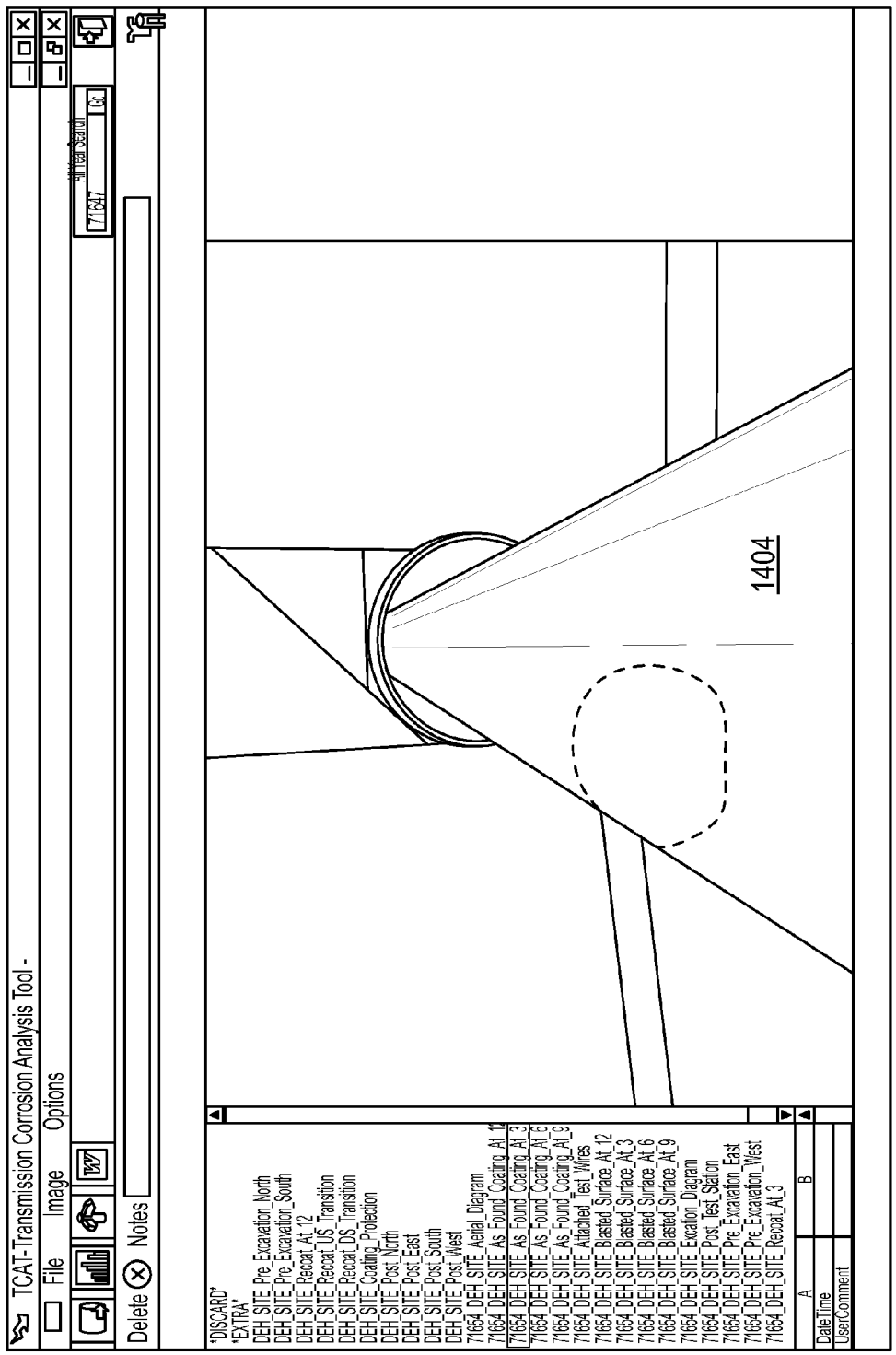

The risk analysis unit 1604 may have a transmission corrosion analysis tool (TCAT™), pipeline version. The TCAT™ allows the workers to acquire, store and manage pipeline related data and timely performance of risk ranking calculations. This may allow for quick identification of pipeline sections/areas with damage and/or the highest risk of damage and timely direction of remediation crews to those high risk pipelines 1404 and/or damaged portion 1426. By way of example only, FIG. 18A through FIG. 18H depict various screenshots of a visual display (with notations added) of the TCAT™ (FIG. 18A representing an example main screenshot allowing user access to secondary screens including bell hole data, anomaly data, anomaly representation, and photos/images; and FIGS. 18B-18H representing various example layers optionally accessible via the main screen including FIG. 18B representing a bell hole data access screen, having drop down selections used to improve data consistency and allowing bell hole data entry; FIG. 18C representing a pipeline anomaly data access screen; FIG. 18D representing a coating anomaly data access screen; FIG. 18E representing an external corrosion cell data access screen; FIG. 18F representing an external corrosion grid data access screen; FIG. 18G representing a pipeline anomaly representation visual and/or data access screen; and FIG. 18H representing a standard set of photos or digital image data access screen wherein a user can zoom into a specific photo by selecting it in the user interface system). The TCAT™ may use an algorithm developed from expertise in corrosion, coating, bell hole, anomaly, etc. science and deployable via measurements. This algorithm integrates numerous data elements, by way of example only, around sixteen electrochemical, chemical, visual and/or physical measurements for the pipeline infrastructure 1402, such as the pipeline 1404, the pipe supports 1428, and/or the like. The algorithm may determine the relative likelihood of corrosion or damage of that pipeline infrastructure 1402. To continually improve the performance of the model, direct information or information used to infer conditions may be integrated, for example, the subsurface direct examination condition data of the interior and/or exterior of the pipeline 1404 may be inputted with direct observations. This allows the TCAT™ model and the assessment team performance to improve in real time as data is collected for a specific assessment project, or implementation project. The TCAT™ model and/or the risk analysis unit 1604 may characterize bell hole data, anomaly data, anomaly representation, visual images all in various forms including soil characteristics, electrochemical factors, electrical interferences, design, cathodic protection, topography, imaging and the like for the pipeline infrastructure 1402.

The data collection unit 1602 may collect all of the data including, but not limited to, input by the field worker 1408 into the one or more data collection tools 1410 and/or the computer 1424. The data collection unit 1602 may then identify important data elements from the collected data. The data collection unit 1602 may then organize, store, categorize, and manipulate the collected data per the needs of the project. The data collection unit 1602 may further keep historical data regarding any of the collected data, data elements, and/or pipeline infrastructure 1402 as the data is collected.

The collected data may further be categorized to determine external corrosion factors for each pipeline 1404 and/or damaged portion(s) 1426a-e of the pipeline. The external corrosion factors may include, but are not limited to, the size of the corrosion at each damaged portion 1426, the depth of the corrosion, the soil conditions, the atmospheric conditions, any conditions described herein, and the like.

The risk analysis unit 1604 may receive information from the data collection unit 1602 to determine risk, or risk factors, in the pipeline infrastructure 1402. The risk analysis unit may have a tool to determine the likelihood that the pipeline 1404 will leak or burst. The risk analysis unit 1604 may determine the extent of actual corrosion and the rate of corrosion since installation of the pipeline 1404. Using the observed and operating conditions of the pipeline, the risk analysis unit 1604 may determine the likelihood of a leak to the pipeline 1404.

The predictive analysis unit 1606 may take the data from the data collection unit 1602, the risk analysis unit 1604 in order to predict the future corrosion of the pipeline 1404. The predictive analysis unit 1606 may generate a corrosion report that details the extent of the actual corrosion, the likelihood of a current pipeline leak, the probability and extent of future corrosion and/or damage, and the likelihood of a pipeline leak in the future.

The mitigation unit 1608 may take the data generated by the predictive analysis unit 1606 and determine which portions of the pipeline infrastructure 1402 need work. The mitigation unit 1608 may determine the type and scale of work to be performed on the pipeline infrastructure 1402. The mitigation unit 1608 may generate a mitigation report detailing the exact location and type of work to be done on the pipeline 1404. The mitigation unit 1608 may recommend any suitable type of work for the pipeline infrastructure 1402 including, but not limited to, painting, applying a protective coating, installing a sleeve over any damaged portion 1426, replacing a portion of the pipeline 1404, any combination thereof, and the like.

The implementation unit 1610 may generate an implementation plan. The implementation plan may determine how soon the work on the pipeline infrastructure 1402 is to be performed and the extent of the work to be performed. For example, if it is determined that there is a probability of a leak in the pipeline 1404, the implementation plan may enact a plan to have that portion of the pipeline infrastructure 1402 fixed immediately. Further, the implementation unit 1610 may determine a time table for future work and maintenance of the pipeline infrastructure 1402 based on the mitigation plan.

All of the functions of the pipeline infrastructure unit 1416 and/or the infrastructure unit 116 may be performed in real time while the field worker is inputting the collected data into the pipeline infrastructure unit 1416 and/or the infrastructure unit 116.

FIGS. 17A-17H depict an example of a report used in conjunction with the pipeline analysis system 1400 according to an embodiment.

The infrastructure unit 116 and/or the pipeline infrastructure unit 1416 may take the form of an entirely hardware embodiment, entirely software embodiment (including firmware, resident software, micro-code, etc.) or an embodiment combining software and hardware aspects. Embodiments may take the form of a computer program embodied in any medium having computer usable program code embodied in the medium. The embodiments may be provided as a computer program product, or software, that may include a machine-readable medium having stored thereon instructions, which may be used to program a computer system (or other electronic device(s)) to perform a process. A machine readable medium includes any mechanism for storing or transmitting information in a form (such as, software, processing application) readable by a machine (such as a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. Embodiments may further be embodied in an electrical, optical, acoustical or other form of propagated signal (e.g., carrier waves, infrared signals, digital signals, etc.), or wireline, wireless, or other communications medium. Further, it should be appreciated that the embodiments may take the form of hand calculations, and/or operator comparisons. To this end, the workers, operator and/or engineer(s) may receive, manipulate, catalog and store the data from the system 100/1400 in order to perform tasks depicted in the infrastructure unit 116 and/or the pipeline infrastructure unit 1416.

While the embodiments are described with reference to various implementations and exploitations, it will be understood that these embodiments are illustrative and that the scope of the inventive subject matter is not limited to them. Many variations, modifications, additions and improvements are possible. For example, the techniques used herein may be applied to any assessment used for structures, bridges, refineries, industrial sites, and the like.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

What is claimed is:

1. A pipeline analysis system, comprising:
 a remote pipeline infrastructure comprising:
  a corrodible pipeline configured to transport fluids;

a plurality of data collection tools configured to collect data from the remote pipeline infrastructure wherein the plurality of data collection tools comprises a camera, a GPS device, a surveying device, a soil tester, a tool for measuring an electrochemical potential of a structure, a tool for measuring corrosion of metal, a pit depth measuring device, a coating measurement device, a soil acidity measuring tool, a soil oxidation-reduction measuring tool, a soil resistivity measuring tool, a caliper, a water pH tester; a nondestructive examination of a structure; and a means for transducing a visual inspection;

a pipeline infrastructure unit configured to receive data from the data collection tools;

wherein the pipeline infrastructure unit comprises:

a data collection unit configured to receive data regarding the remote pipeline infrastructure from the data collection tools;

a risk analysis unit configured to evaluate a corrosion condition of the corrodible pipeline based on the received data;

a predictive analysis unit responsive to the data collection unit and the risk analysis unit configured to generate a corrosion report detailing actual corrosion, a likelihood of a current pipeline leak and a probability of future corrosion;

a mitigation unit configured to determine a type of mitigation work to be performed on the corrodible pipeline; and an implementation unit configured to assess the relative risk to the remote pipeline infrastructure and create and execute an implementation plan for remediation of the remote pipeline infrastructure.

2. The pipeline analysis system according to claim 1, wherein the plurality of data collection tools additionally comprises a pig.

3. The pipeline analysis system according to claim 1, wherein the plurality of data collection tools further comprises a scanner, an acoustic tool, a pressure monitor, and a flow meter.

4. The pipeline analysis system according to claim 1, further comprising the step of electronically storing all the received data gathered from the remote pipeline infrastructure for accessing and manipulating the received data at a future point in time.

5. The pipeline analysis system according to claim 1, further comprising the step of inputting the received data associated with the remote pipeline infrastructure into a computer located at the remote pipeline infrastructure.

6. A pipeline analysis system, comprising:

a remote pipeline infrastructure comprising:

a corrodible pipeline configured to transport fluids;

a plurality of data collection tools configured to collect data from the remote pipeline infrastructure wherein the plurality of data collection tools comprises a camera, a GPS device, a surveying device, a soil tester, a tool for measuring an electrochemical potential of a structure, a tool for measuring corrosion of metal, a pit depth measuring device, a coating measurement device, a soil acidity measuring tool, a soil oxidation-reduction measuring tool, a soil resistivity measuring tool, a caliper, a water pH tester, a nondestructive examination of a structure; and a means for transducing a visual inspection;

a pipeline infrastructure unit configured to receive data from the data collection tools;

wherein the pipeline infrastructure unit comprises:

a data collection unit configured to receive data regarding the remote pipeline infrastructure from the data collection tools;

a risk analysis unit configured to evaluate a corrosion condition of the corrodible pipeline based on the received data;

a predictive analysis unit responsive to the data collection unit and the risk analysis unit configured to generate a corrosion report detailing actual corrosion, a likelihood of a current pipeline leak and a probability of future corrosion;

a mitigation unit configured to determine a type of mitigation work to be performed on the corrodible pipeline; and an implementation unit configured to assess the relative risk to the remote pipeline infrastructure and create an implementation plan for remediation of the remote pipeline infrastructure; and further comprising the step of executing the implementation plan for repairing the corrodible pipeline of the remote pipeline infrastructure.

* * * * *